US011524956B2

(12) United States Patent
Shen et al.

(10) Patent No.: US 11,524,956 B2
(45) Date of Patent: *Dec. 13, 2022

(54) ALKYNE SUBSTITUTED QUINAZOLINE COMPOUND AND METHODS OF USE

(71) Applicant: Newgen Therapeutics, Inc., Menlo Park, CA (US)

(72) Inventors: Wang Shen, San Mateo, CA (US); Aimin Zhang, Castro Valley, CA (US); Jack Maung, Daly City, CA (US); Xiaoling Zheng, Fremont, CA (US)

(73) Assignee: Newgen Therapeutics, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/833,020

(22) Filed: Mar. 27, 2020

(65) Prior Publication Data

US 2021/0047303 A1  Feb. 18, 2021

Related U.S. Application Data

(63) Continuation of application No. 16/252,458, filed on Jan. 18, 2019, now abandoned, which is a continuation of application No. 15/675,438, filed on Aug. 11, 2017, now abandoned, which is a continuation of application No. 14/745,308, filed on Jun. 19, 2015, now abandoned, which is a continuation of application No. 14/002,983, filed as application No. PCT/US2012/027614 on Mar. 2, 2012, now Pat. No. 9,090,588.

(60) Provisional application No. 61/449,088, filed on Mar. 4, 2011.

(51) Int. Cl.
*A61K 31/517* (2006.01)
*C07D 405/06* (2006.01)

(52) U.S. Cl.
CPC .......... *C07D 405/06* (2013.01); *A61K 31/517* (2013.01)

(58) Field of Classification Search
CPC .................................................. C07D 405/06
See application file for complete search history.

(56) References Cited

U.S. PATENT DOCUMENTS

| | | |
|---|---|---|
| 4,062,881 A | 12/1977 | Kugele |
| 4,343,940 A | 8/1982 | Kreighbaum et al. |
| 5,053,227 A | 10/1991 | Chiang et al. |
| 5,457,105 A | 10/1995 | Barker |
| 5,475,001 A | 12/1995 | Barker |
| 5,521,884 A | 5/1996 | Humphries et al. |
| 5,586,870 A | 12/1996 | Kawaguchi et al. |
| 5,616,582 A | 4/1997 | Barker |
| 5,747,498 A | 5/1998 | Schnur |
| 5,770,599 A | 6/1998 | Gibson |
| 6,225,318 B1 | 5/2001 | Sobolov-jaynes et al. |
| 6,391,874 B1 | 5/2002 | Cockerill |
| 6,414,148 B1 | 7/2002 | Thomas et al. |
| 6,627,634 B2 | 9/2003 | Himmelsbach et al. |
| 6,713,485 B2 | 3/2004 | Carter et al. |
| 6,727,256 B1 | 4/2004 | Carter et al. |
| 6,828,320 B2 | 12/2004 | Cockerill et al. |
| 6,894,051 B1 | 5/2005 | Zimmermann et al. |
| 6,900,221 B1 | 5/2005 | Norris et al. |
| 6,958,335 B2 | 10/2005 | Buchdunger et al. |
| 7,157,466 B2 | 1/2007 | Mcclure et al. |
| 9,090,588 B2 * | 7/2015 | Shen ..................... A61P 43/00 |
| 9,187,459 B2 | 11/2015 | Shen et al. |
| 9,730,934 B2 | 8/2017 | Huang et al. |
| 2004/0116422 A1 | 6/2004 | Kitano et al. |
| 2006/0089382 A1 | 4/2006 | Hennequin et al. |
| 2006/0155412 A1 | 7/2006 | Ikeda |
| 2006/0270668 A1 | 11/2006 | Chew et al. |
| 2008/0249087 A1 | 10/2008 | Rotstein et al. |
| 2008/0269487 A1 | 10/2008 | Bradbury et al. |
| 2009/0306044 A1 | 12/2009 | Solca et al. |
| 2014/0128417 A1 | 5/2014 | Shen et al. |
| 2014/0221406 A1 | 8/2014 | Shen et al. |
| 2016/0031860 A1 | 2/2016 | Shen et al. |
| 2018/0093975 A1 | 4/2018 | Shen et al. |
| 2019/0382382 A1 | 12/2019 | Shen et al. |

FOREIGN PATENT DOCUMENTS

| | | |
|---|---|---|
| CN | 1182421 A | 5/1998 |
| CN | 1292788 A | 4/2001 |
| CN | 1310713 A | 8/2001 |
| CN | 1134430 C | 1/2004 |
| CN | 1656081 A | 8/2005 |
| CN | 1812051 A | 8/2006 |
| CN | 1817895 A | 8/2006 |
| CN | 1867564 A | 11/2006 |
| CN | 1305872 C | 3/2007 |
| EP | 0326307 A2 | 8/1989 |

(Continued)

OTHER PUBLICATIONS

Vlppagunta et al. (2001).*
Pinedo et al. (2000).*
McMahon et al. (2000).*
Banker, G. et al. (1997). Modern Pharmaceuticals, 3 pages.
Baselga, J. et al. (Jul. 2009). "Novel Anticancer Targets: Revisiting ERBB2 and Discovering ERBB3," Nature Reviews 9:463-473.
Bendell et al. (Jun. 15, 2003). "Central Nervous System Metastases in Women who Receive Trastuzumab-Based Therapy for Metastatic Breast Carcinoma," Cancer, 97(12):2972-2977.
Blackhall et al. (2005). "Erlotinib in Non-small Cell Lung Cancer: A Review," Expert Opinion on Pharmacotherapy, 6(6):995-1002.
Bordoni, I. et al. (2011). "Afatinib (BIBW-2992): A Novel Dual EGFR/HER2neu Inhibitor with Promising Activity in Non-Small-Cell Lung Cancer," Therapy, 8(1):15-22.

(Continued)

*Primary Examiner* — Paul V Ward
(74) *Attorney, Agent, or Firm* — Morrison & Foerster LLP

(57) ABSTRACT

The invention provides alkyne substituted quinazoline compounds, such as compounds of the formula (I), which are irreversible ErbB kinase inhibitors. The compounds are useful in the treatment of diseases and disorders where ErbB kinase activity is implicated such as a hyperproliferative disorder (e.g., cancer).

55 Claims, 4 Drawing Sheets

(56) References Cited

FOREIGN PATENT DOCUMENTS

| | | |
|---|---|---|
| EP | 1369418 B1 | 7/2010 |
| GB | 2160201 A | 12/1985 |
| JP | 2006501185 A | 1/2006 |
| JP | 2008545688 A | 12/2008 |
| JP | 4285996 B2 | 4/2009 |
| JP | 2009515851 A | 4/2009 |
| KR | 102061743 B1 | 1/2020 |
| WO | 199521613 A1 | 8/1995 |
| WO | 199524190 A2 | 9/1995 |
| WO | 199524190 A3 | 11/1995 |
| WO | 199629331 A1 | 9/1996 |
| WO | 199630347 A1 | 10/1996 |
| WO | 199634867 A1 | 11/1996 |
| WO | 199635689 A1 | 11/1996 |
| WO | 199639145 A1 | 12/1996 |
| WO | 199640142 A1 | 12/1996 |
| WO | 199640648 A1 | 12/1996 |
| WO | 199702266 A1 | 1/1997 |
| WO | 199703069 A1 | 1/1997 |
| WO | 199713760 A1 | 4/1997 |
| WO | 199713771 A1 | 4/1997 |
| WO | 199738973 A1 | 10/1997 |
| WO | 199903854 A1 | 1/1999 |
| WO | 199909016 A1 | 2/1999 |
| WO | 199935146 A1 | 7/1999 |
| WO | 200006555 A1 | 2/2000 |
| WO | 200202552 A1 | 1/2002 |
| WO | 200250043 A1 | 6/2002 |
| WO | 2002066445 A1 | 8/2002 |
| WO | 2004005284 A1 | 1/2004 |
| WO | 2004006846 A2 | 1/2004 |
| WO | 2004006846 A3 | 7/2004 |
| WO | 2005037824 A2 | 4/2005 |
| WO | 2005037824 A3 | 7/2005 |
| WO | 2006127207 A1 | 11/2006 |
| WO | 2007054550 A1 | 5/2007 |
| WO | 2007085638 A1 | 8/2007 |
| WO | 2008033749 A2 | 3/2008 |
| WO | 2008033749 A3 | 12/2008 |
| WO | 2009140863 A1 | 11/2009 |
| WO | 2011084796 A2 | 7/2011 |
| WO | 2012021591 A1 | 2/2012 |
| WO | 2012027960 A1 | 3/2012 |
| WO | 2012155339 A1 | 11/2012 |
| WO | 2012158979 A1 | 11/2012 |

OTHER PUBLICATIONS

Bose et al. (2009). "Neratinib: All Oral, Irreversible Dual EGFR/HER2 Inhibitor for Breast and Non-Small Cell Lung Cancer," Expert Opinion on Investigational Drugs, 18(11):1735-1751.
Brennan et al. (2000). "HER2/Neu: Mechanisms of Dimerization/oligomerization", Oncogene, 19:6093-6101.
Bridges, A.J. et al. (1995). "Enantioselective Inhibition Of The Epidermal Growth Factor Receptor Tyrosine Kinase By 4-(α-Phenethylamino) Quinazolines," Bioorganic & Medicinal Chemistry, 3(12):1651-1656.
Broniscer et al. (2007). "Plasma and Cerebrospinal Fluid Pharmacokinetics of Erlotinib and Its Active Metabolite OSI-420," Clinical Cancer Research, 13(5):1511-1515.
Burgess, A.W. (2008). "EGFR Family: Structure Physiology Signalling and Therapeutic Targets," Growth Factors, 26(5):263-274.
Canadian Office Action, dated Jan. 18, 2019, for Canadian Patent Application No. 2828713, 4 pages.
Cha et al. (2009). "Discovery of A Novel Her-1/Her-2 Dual Tyrosine Kinase Inhibitor for the Treatment of Her-1 Selective16 Inhibitor-Resistant Non-small Cell Lung Cancer," Journal of Medicinal Chemistry, 52(21):6880-6888.
Cho, A. (2006). "Recent Advances in Oral Prodrug Discovery," Annual Reports in Medicinal Chemistry, 41:395-407.
Doebele et al. (2010). "New Strategies to Overcome Limitations of Reversible EGFR Tyrosine Kinase Inhibitor Therapy in Non-Small Cell Lung Cancer," Lung Cancer, 69:1-12.

Eichler et al. (2010). "EGFR Mutation Status and Survival after Diagnosis of Brain Metastasis in Nonsmall Cell Lung Cancer," Neuro-Oncology, 12(11):1193-1199.
European Article 97(1), mailed Apr. 26, 2018, for European Application No. 12754325.4, 2 pages.
European Examination Report dated Nov. 6, 2015, for European Patent Application No. 12786332.2, 4 pages.
Extended European Search Report (includes Supplementary European Search Report and Search Opinion) received for European Patent Application No. 12754325.4, dated Jan. 9, 2015, 8 pages.
Extended European Search Report (includes Supplementary European Search Report and Search Opinion) received for European Patent Application No. 12786332.2, dated Oct. 21, 2014, 6 pages.
Heitz et al. (2011). "Cerebral Metastases in Metastatic Breast Cancer: Disease-Specific Risk Factors and Survival," Annals of Oncology, 22:1571-1581.
Hynes et al. (1994). "The Biology of ErbB-2/nue/HER-2 and its Role in Cancer," Biochemical et Biophysical Acta, 1198:165-184.
International Preliminary Report On Patentability received for PCT Patent Application No. PCT/CN2011/074165, dated Nov. 19, 2013, 15 pages (7 pages of English Translation and 8 pages of Official Copy).
International Preliminary Report On Patentability received for PCT Patent Application No. PCT/US2012/027614, dated Mar. 12, 2014, 6 pages.
International Preliminary Report On Patentability received for PCT Patent Application No. PCT/US2012/038458, dated Nov. 19, 2013, 8 pages.
International Search Reports Written Opinion received for PCT Patent Application No. PCT/CN2011/074165, dated Mar. 8, 2012, 24 pages (12 pages of English Translation and 12 pages of Official Copy).
International Search Report & Written Opinion received for PCT Patent Application No. PCT/US2012/027614, dated Jun. 8, 2012, 8 pages.
International Search Report & Written Opinion received for PCT Patent Application No. PCT/US2012/038458, dated Jul. 25, 2012, 11 pages.
Klapper et al. (2000). "Biochemical and Clinical Implications of the ErbB/HER Signaling Network of Growth Factor Receptors," Advanced Cancer Research, 77:25-79.
Lassman et al. (Nov. 21, 2005). "Molecular Study of Malignant Gliomas Treated with Epidermal Growth Factor Receptor Inhibitors: 23 Tissue Analysis from North American Brain Tumor Consortium Trials 01-03 and 00-01", Clinical Cancer Research, 11:7841-7850.
Lemmon, M.A. (Feb. 15, 2009). "Ligand-Induced ErbB Receptor Dimerization," Experimental Cell Research, 315(4):638-648.
Li et al. (2008). "BIBW2992, An irreversible EGFR/HER2 Inhibitor Highly Effective in Preclinical Lung Cancer Models," Oncogene, 27(34):4702-4711.
McMahon, S.B. et al. (Jan. 2000). "The Essential Cofactor TRRAP Recruits the Histone Acetyltransferase hGCN5 to c-Myc," Molecular and Cellular Biology 20(2):556-562.
Milanezi et al. (Nov. 4, 2008). "EGFRJHER2 in Breast Cancer: a Biological Approach for Molecular Diagnosis and Therapy," Expert Review of Molecular Diagnostics, 8(4):417-434.
Minkovsky et al. (Dec. 2008). "BIBW-2992, A Dual Receptor Tyrosine Kinase Inhibitor for the Treatment of Solid Tumors," Current Opinion in Investigational Drugs, 9(12):1336-1346.
Moon et al. (2007). "Synthesis of Enantiopure Pseudo-1-Vinylcyclopropyl Nucleosides Bearing Quaternary Carbon as Potential Anti-Herpesvirus Agent", Nucleosides, Nucleotides and Nucleic Acids, 26:975-978.
Müller et al. (Jun. 1996). "An Improved One-pot Procedure for the Synthesis of Alkynes from Aldehydes," Synlett, pp. 521-522.
Non-Final Office Action for U.S. Appl. No. 14/745,308, dated Feb. 13, 2017, filed Jun. 19, 2015.
Non-Final Office Action for U.S. Appl. No. 15/675,438, dated Jul. 19, 2018, filed Aug. 11, 2017, 18 pages.
O'Donovan et al. (2007). "EGFR and HER-2 Antagonists in Breast Cancer," Anticancer Research, 27:1285-1294.

(56) References Cited

OTHER PUBLICATIONS

Ocaña et al. (2009). "Irreversible Pan-ErbB Tyrosine Kinase Inhibitors and Breast Cancer: Current Status and Future Directions," Cancer Treatment Reviews, 35:685-691.

Office Action received for Taiwan Patent Application No. 101117618, dated Aug. 7, 2015, 7 pages, (with English translation of the attached Search Report).

Ohira, S. (1989). "Methanolysis of Dimethyl {1-Diazo-2-oxopropyl) Phosphonate: Generation of Dimethyl (Diazomethyl) Phosphonate and Reaction with Carbonyl Compounds," Synthetic Communications, 19(3&4):561-564.

Ostrowski et al. (2006). "Synthesis and Biological Activity of Tricyclic Analogues of 9-{[cis-1', 2'-bis(Hydroxymethyl) Cycloprop-1'-yl]methyl}guanine," Bioorganic & Medicinal Chemistry, 14:3535-3542.

Pinedo, H.M. et al. (2000). "Translational Research: The Role of VEGF in Tumor Angiogenesis," The Oncologists (Suppl. 1):1-2.

Reid et al. (2007). "Dual inhibition of ErbB1 (EGFRJHER1) and ErbB2 {HER2/neu)," European Journal of Cancer, 43:481-489.

Rewcastle et al. (1996). "Tyrosine Kinase Inhibitors. 9. Synthesis and Evaluation of Fused Tricyclic Quinazoline Analogues as ATP Site Inhibitors of the Tyrosine Kinase Activity of the Epidermal Growth Factor Receptor," Journal of Medicinal Chemistry, 39:918-928.

Sakai et al. (2008). "Direct Reduction of Esters to Ethers with an Indium{III) Bromide!Triethylsilane Catalytic System," Synthesis, 21:3533-3536.

Salomon et al. (1995). "Epidermal Growth Factor-Related Peptides and their Receptors in Human Malignancies," Critical Reviews in Oncology/Hematology, 19:183-232.

Smaill et al. (2000). "Tyrosine Kinase Inhibitors. 17. Irreversible Inhibitors of the Epidermal Growth Factor Receptor: 4-(Phenylamino)quinazoline- and 4-(Phenylamino) pyrido[3,2-d)pyrimidine-6-acrylamides Bearing Additional Solubilizing Functions," Journal of Medicinal Chemistry, 43:1380-1397.

Smith et al. (2007). Chapter 4 of March's Advanced Organic Chemistry: Reactions, Mechanisms and Structure, John Wiley & Sons. 6th edition, 118 pages.

Steeg et al. (May 2011). "Brain Metastases as Preventive and Therapeutic Targets," Nature Reviews Cancer, 11:352-363.

Stella et al. (2007). Prodrugs: Challenges and Rewards, Part 1, American Association of Pharmaceutical Scientists, 10 pages.

Tsou et al. (2005). "Optimization of 6,7-Disubstituted-4-(arylamino)Quinoline-3-Carbonitriles as Orally Active, Irreversible7 Inhibitors of Human Epidemial Growth Factor Receptor-2 Kinase Activity", Journal of Medicinal Chemistry, 48(D4):1107-1131.

Vippagunta, S.R. et al. (2001). "Crystalline Solids," Advanced Drug Delivery Reviews 48:3-26.

Wolff et al. (1997). Burger's Medicinal Chemistry, pp. 975-977.

Zhang et al. (2007). "ErbB Receptors: from Oncogenes to Targeted Cancer Therapies," The Journal of Clinical Investigation, D 117(8):2051-2058.

Australian Office Action, dated May 16, 2019, for Australian Patent Application No. 2018267622, 3 pages.

\* cited by examiner

US 11,524,956 B2

ALKYNE SUBSTITUTED QUINAZOLINE COMPOUND AND METHODS OF USE

CROSS-REFERENCE TO RELATED APPLICATIONS

This application is a continuation of U.S. patent application No. 16/252,458, filed Jan. 18, 2019, which is a continuation of U.S. patent application No. 15/675,438, filed Aug. 11, 2017, now abandoned, which is a continuation of U.S. patent application No. 14/745,308, filed Jun. 19, 2015, now abandoned, which is a continuation of U.S. patent application No. 14/002,983, which adopts the international filing date of Mar. 2, 2012, and is issued as U.S. Pat. No. 9,090,588, which is a National Phase filing under 35 U.S.C. § 371 of International Application No. PCT/US2012/027614 having an international filing date of Mar. 2, 2012, which claims priority to U.S. Provisional Patent Application No. 61/449,088 filed Mar. 4, 2011, the disclosures of which are incorporated herein by reference in their entireties.

FIELD OF THE INVENTION

The invention relates to novel quinazoline derivatives containing alkyne moieties as irreversible inhibitors of type I receptor protein kinase. These inhibitors are useful in treating disorders related to abnormal protein kinase activities such as cancer and inflammation in mammals. The invention also relates to the pharmaceutical composition containing these inhibitors, methods for the preparation of these inhibitors and their pharmaceutically acceptable salts.

BACKGROUND OF THE INVENTION

The type I receptor tyrosine kinase family is comprised of four closely related receptors: ErbB1 (EFGR or HER1), ErbB2 (HER2), ErbB3 (HER) and ErbB4 (HER4). These receptors are transmembrane glycoproteins which contain an extracellular domain for ligand binding and, with the exception of HERS, an intracellular catalytically active tyrosine kinase domain. These receptors transmit extracellular signals through the cytosol via a signal transduction cascade to the nucleus. The extracellular signal is transmitted by ligand binding to the dimeric receptor, with the exception of erbB2, of which a high affinity soluble ligand has yet to be identified. After ligand binding, the type I receptor tyrosine kinases either homodimerize or heterodimerize with another member of the subfamily of receptors (Lemmon M A, Experiment. Cell Res. (2009), 315:638-648). ErbB2 participates in this process by heterodimerization and is the preferred heterodimerization partner (Brennan P J, et al., Oncogene (2000), 19:6093). Dimerization leads to activation of the ErbB receptors by autophosphorylation of the intracellular domain. This autophosphorylation recruits adaptor proteins and leads to a phosphorylation cascade that transmits the signal throughout the cell. The type I receptor tyrosine kinase family (ErbB family) signals through the ras/raf/MEK/MAPK pathway as well as the PI3K/Akt pathway. These signaling pathways lead to both cell proliferation and cell survival through inhibition of apoptosis.

ErbB family receptors play important roles in cancer (Burgess A W, Growth Factors (2008), 26:263-74). Squamous carcinomas of the head and neck, and lung express high levels of EGFR. Also, constitutively active EGFR has been found in gliomas, breast cancer and lung cancer (Salomon, et al., Critical Rev. Oncol. Hematol. (1995), 19:183-232; Mapper, et al., Adv. Cancer Res. (2000), 77:25- 79, and Hynes and Stern, Biochimica Biophysica Acta (1994), 1198:165-184). ErbB2 overexpression occurs in approximately 30% of all breast cancer (Milanezi, et al., Expert Rev. Mo. Diagnosis. (2008), 8(4), 417-34). ErbB2 is also implicated in other human cancers including colon, ovary, bladder, stomach, esophagus, lung, uterus and prostate. ErbB2 overexpression correlates with poor prognosis in human cancer, including metastasis, and early relapses (Baselga J and Swain S M, Nature Rev. Cancer (2009), 9:463-75).

The type I tyrosine kinase receptor family has been an active area of anti-cancer research (O'Donovan and Crown, Anticancer Res. (2007) 27(3A):1285-94). Several inhibitors of the EGFR and the ErbB2 signaling pathway have demonstrated clinical efficacy in cancer treatment. Herceptin, a humanized version of anti-ErbB2 monoclonal antibody, and panitumumab and cetuximab, two anti-EGFR monoclonal antibodies were approved for use in breast, colorectal, and head and neck cancers in the United States recently. Gefitinib (Iressa®) and erlotinib (Tarceva®) are small molecule inhibitors of EGFR that were launched for the treatment of certain solid cancers including lung cancer. In addition, lapatinib, a dual inhibitor of EGFR and ErbB2 was approved by FDA for treatment of metastatic breast cancer in 2007. A number of other antibodies and small molecules that target the interruption of the type I tyrosine kinase receptor signaling pathways are in clinical and preclinical development (Zhang, et al 0.1. Clin. Investigation (2007), 117:2051-2058), including some irreversible dual inhibitors of ErbB1, ErbB2 (Minkovsky N, Berezov A. Curr. Opin. Investig. Drugs. (2008); 9:1336-46; Bose P. Ozer H. Expert Opin. Investig. Drugs. (2009); 18:1735-51).

One significant unmet medical needs is the new treatment for primary brain tumor, particularly glioblastoma multiforme (GBM). A large percentage of GBM brain tumors harbors a disease-driving EGFR imitation, EGFRvIII. However, currently available EGFR small molecule inhibitors (erlotinib and gefitinib) and antibodies (cetuximab and panitumumab) have limited exposure in the brain due to their inefficiency to cross blood-brain-barrier (BBB) (Broniscer, et al., Clin. Cancer Res. (2007):1511; Lassman, et al., Clin. Cancer Res. 2005:7841). Therefore, they cannot be used for the treatment of GBM.

The incidence of metastasis to the brain is increasing in cancer patients, especially from the lung cancer, breast cancer and melanoma. The brain is considered a 'sanctuary site' as the blood-tumor barrier limits the ability of drugs to enter and kill tumor cells (Steeg, P S; et al., Nat. Rev. Cancer (2011) 11:352). Brain metastases from lung cancer account for 40-50% of all brain metastases, and close to half of these lung cancer brain metastases harbor EGFR mutations (Eichler, A F, et al., Neuro-Oncology (2010), 12:1193). Similarly, while use of Herceptin has significantly improved the outcome of HER2 positive breast cancer patients many of these breast cancer patients developed brain metastases while being treated by Herceptin (http://www.cityofhope.org/eHope, 11(2) Feb. 21, 2012; Heitz, F.; et al., Ann, Oncol. (2011) 22:1571; Bendell, J. et al., Cancer (2003) 97:2972).

There is a continuing need for new cancer treatment and a significant medical need for compounds capable of treating tumors in the brain.

BRIEF SUMMARY OF THE INVENTION

This invention provides for alkynyl substituted 4-anilino quinazolines of the formula (I) or any variations detailed herein, and pharmaceutically acceptable salts and prodrugs thereof, that are useful in the treatment of hyperproliferative diseases, such as cancer. Specifically, the present invention relates to compounds of the formula (I), or any variations detailed herein, that act as EGFR and ErbB2 inhibitors. Also provided are formulations containing compounds of the formula (I) and methods of using the compounds in treating n individual in need thereof. In addition, described are processes for preparing the inhibitory compounds of the formula (I).

In one aspect, provided is a compound of the formula (I):

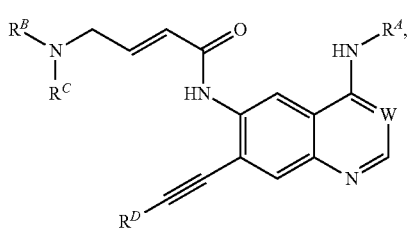

or a salt, solvate, or physiologically functional derivative thereof, wherein:

W is N or C—CN;

$R^A$ is a substituted aryl or substituted heteroaryl;

each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with 1 to 3 groups independently selected from the group consisting of oxo, halogen and —$OR^1$; or $R^B$ and $R^C$ are taken together with the nitrogen atom to which they are attached to form a 4 to 7-membered heterocyclyl, which is optionally substituted with up to 3 groups independently selected from the group consisting of halogen, oxo, —$OR^1$, —$NR^2R^3$, $C_1$-$C_3$ alkyl and $C_3$-$C_6$ cycloalkyl;

$R^D$ is a heterocyclyl containing 1-3 hetero ring atoms selected from "O", "N", "S", S(O)", or "S(O)$_2$", where the heterocyclyl is optionally substituted with 1 to 3 groups independently selected from halogen, oxo, —$OCF_3$, —$CF_3$, —$NR^2R^3$, $C_1$-$C_3$ alkyl and $C_3$-$C_6$ cycloalkyl; and each $R^1$, $R^2$ and $R^3$ is independently selected from H and $C_1$-$C_3$ alkyl.

In some embodiments, the compound is of the formula (I), or salt, solvate, or physiologically functional derivative thereof, wherein W is N, $R^A$ is 3-chloro-4-fluorophenyl, each $R^B$ and $R^C$ is methyl, and $R^D$ is a tetrahydrofuanyl, 3-oxabicyclo[3.1.0]hexan-6-yl or 3-oxabicyclo[3.1.0]hexan-1-yl. In a particular variation, $R^D$ is 3-oxabicyclo[3.1.0]hexan-6-yl.

In another aspect, provided are methods for treating a hyperproliferative disorder in an individual in need thereof comprising administering to the individual an effective amount of a compound of the formula (I), or salt, solvate, or physiologically functional derivative thereof. In some embodiments, the hyperproliferative disorder is a tumor in the brain such as a primary brain tumor (e.g., glioma and GBM) or a metastatic brain tumor (e.g., brain metastasis of breast cancer or lung cancer).

The invention also provides pharmaceutically acceptable salts, pharmaceutically acceptable prodrugs, and pharmaceutically active metabolites of the compound of the formula (I) or any variations described herein. Methods of making the compounds of the formula (I) are also described.

Also provided are pharmaceutical compositions comprising a compound detailed herein such as a compound of the formula (I), or a pharmaceutically acceptable prodrug, pharmaceutically active metabolite, or pharmaceutically acceptable salt thereof, and a pharmaceutically acceptable carrier or excipient. Compounds as detailed herein or a pharmaceutically acceptable salt thereof are also provided for the manufacture of a medicament for the treatment of cancer. Kits comprising a compound detailed herein are provided, which optionally includes instructions for use in the methods detailed herein (e.g., in treating a hyperproliferative disorder including brain tumors).

It is to be understood that one, some, or all of the features of the various embodiments described herein may be combined to form other embodiments of the present invention. These and other aspects of the invention will become apparent to one of skill in the art.

DETAILED DESCRIPTION OF THE INVENTION

Figure 1:
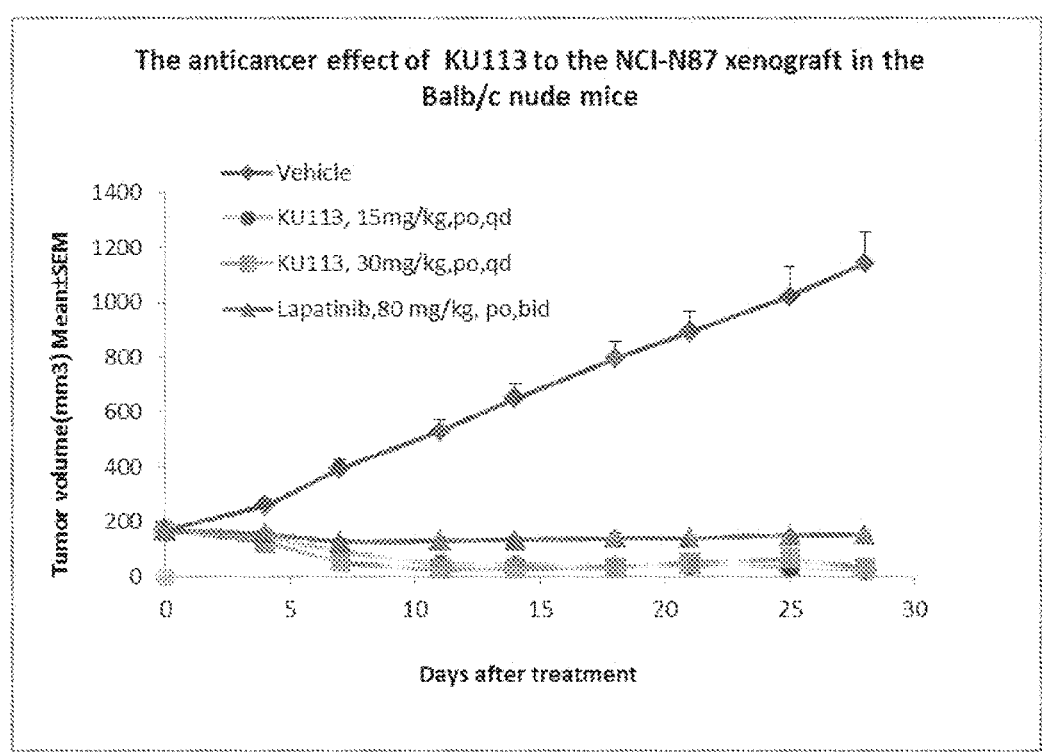
FIG. 1 shows the anticancer effect of Compound KU113 to the NCI-N87 xenograft in the Balb/c nude mice. The structure of Compound KU113, also referred to as "NT113", is described in Example 4.

This invention provides compounds that are inhibitors of EGFR and HER2 kinases, and are capable of crossing the blood-brain-barrier. Compounds and compositions provided herein having durable exposure in brain can help patients suffering from brain cancers, who currently have limited options of effective therapies.

Definitions

Except as expressly defined otherwise, the following definition of terms is employed throughout this specification.

The term "alkyl" as used herein refers to a saturated linear or branched-chain hydrocarbon of one to twelve carbon atoms, wherein the alkyl radical may be independently substituted with one or more substituents described below. Examples of alkyl groups include, hut are not limited to, methyl, ethyl, n-propyl, isopropyl, butyl, isobutyl, sec-butyl, tert-butyl, pentyl, isopentyl, tert-pentyl, hexyl, isohexyl, and the like. More preferred alkyl radicals have 1 to 8 carbon atoms ("$C_1$-$C_8$ alkyl"). More preferred alkyl radicals have 1 to 4 carbon atoms ("$C_1$-$C_4$ alkyl").

The term "alkenyl" refers to linear or branched-chain hydrocarbon radical of two to twelve carbon atoms, containing at least one double bond, such as ethenyl, propenyl, and the like, wherein the alkenyl radical may be optionally substituted independently with one or more substituents described herein, and includes radicals having "cis" and "trans" orientations, or alternatively, "E" and "Z" orientations. The preferred alkenyl radicals are those with 2 to 6 carbon atoms ("$C_2$-$C_6$ alkenyl").

The term "alkynyl" refers to a linear or branched hydrocarbon radical of two to twelve carbon atoms containing at least one triple bond. Examples include ethynyl, propynyl, and the like, wherein the alkynyl radical may be optionally substituted independently with one or more substituents described herein. Preferred alkynyl radicals are those having 2 to 6 carbon atoms ("$C_1$-$C_6$ alkynyl").

The term "cycloalkyl" refers to saturated or partially unsaturated cyclic hydrocarbon radical having from three to twelve carbon atoms, wherein the cycloalkyl may be optionally substituted independently with one or more substituents described herein. "Cycloalkyl" further includes spirocyclic, bicyclic and tricyclic cycloalkyl structures, wherein the bicyclic and tricyclic structures may include a saturated or partially unsaturated cycloalkyl fused to a saturated or partially unsaturated cycloalkyl or heterocycloalkyl ring or an aryl or heteroaryl ring. Spiro moieties are also included within the scope of this definition. Preferred cycloalkyl groups are those with 3 to 8 carbon atoms ("$C_3$-$C_8$ cycloalkyl"). More preferred cycloalkyl groups are those with 3 to 6 carbon atoms ("$C_3$-$C_6$ cycloalkyl"). Examples of cycloalkyl groups include, but are not limited to, cyclopropyl, cyclobutyl, cyclopentyl, cyclohexyl, cycloheptyl, adamantyl, norbornyl and the like.

The term "heteroalkyl" refers to saturated or partially unsaturated linear or branched-chain hydrocarbon radical of one to twelve carbon atoms, wherein at least one of the carbon atoms is replaced with a heteroatom selected from N, O, or S, and wherein the radical may be a carbon radical or heteroatom radical (i.e., the heteroatom may appear in the middle or at the end of the radical). The heteroatom may be oxized, such as $S(O)$ and $S(O)_2$. A heteroalkyl radical may be optionally substituted independently with one or more substituents described herein. The term "heteroalkyl" encompasses alkoxy and heteroalkoxy radicals.

The term "heterocyclyl" refers to a saturated or partially saturated cyclic radical of 3 to 14 ring atoms in which at least one ring atom is a heteroatom selected from nitrogen, oxygen and sulfur, the remaining ring atoms being carbon where one or more ring atoms may be optionally substituted independently with one or more substituent described herein. The radical may be a carbon radical or heteroatom radical. "Heterocyclyl" also includes radicals where heterocycle radicals are fused with aromatic or heteroaromatic rings. A "heterocyclyl" may be mono-cyclic, bicyclic, multi-cyclic. Spiro moieties are also included within the scope of this definition. Examples of "heterocyclyl" include, but are not limited to, pyrrolidinyl, piperidinyl, piperazinyl, tetrahydrofuranyl, tetrahydropyranyl, morpholinyl, thiomorpholinyl, homopiperazinyl, phthalimidyl, 3-oxabicyclo[3.1.0]hexyl 3-oxabicyclo[3.1.0]hexan-6-yl and 3-oxabicyclo[3.1.0]hexan-1-yl), and derivatives thereof.

The term "aryl" refers to an aromatic carbocyclic group having a single ring (e.g., phenyl), multiple rings (e.g., biphenyl), or multiple condensed rings in which at least one is aromatic, (e.g., 1,2,34-tetrahydronaphthyl, naphthyl), which is optionally mono-, di-, or trisubstituted with, e.g., halogen, lower alkyl, lower alkyloxy, trifluoromethyl, aryl, heteroaryl, and hydroxy.

"Heteroaryl" means a monocyclic aromatic radical of 5 to 10 ring atoms or a polycyclic aromatic radical, containing one or more ring heteroatoms selected from nitrogen, oxygen, or sulfur, the remaining ring atoms being carbon. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Other non-limiting examples of heteroaryl include triazolo[1,5-a]pyridinyl, imidazo[1,2-a]pyridinyl and indazolyl.

The term "halo" represents fluoro, chloro, bromo or iodo. Likewise, the term "halogen" refers to a fluorine, chlorine, bromine, or iodine substituent.

The term "substituted" refers to the replacement of one or more hydrogen atoms of a moiety with a monovalent or divalent radical, "Optionally substituted" indicates that the moiety may be substituted or unsubstituted. A moiety lacking the terms "optionally substituted" and "substituted" is intended an unsubstituted moiety (e.g., "phenyl" is intended an unsubstituted phenyl unless indicated as a substituted phenyl or an optionally substituted phenyl).

As used herein, "treatment" or "treating" is intended to mean at least the mitigation of a disease condition in a mammal, such as a human, that is affected, at least in part, by the activity of one or more ErbB family tyrosine kinases and/or serine, threonine kinases, and includes, but is not limited to, preventing the disease condition from occurring in a mammal, particularly when the mammal is found to be predisposed to having the disease condition but has not yet been diagnosed as having it; modulating and/or inhibiting the disease condition; and/or alleviating the disease condition.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "in conjunction with" refers to administration of one treatment modality in addition to another treatment modality. As such, "in conjunction with" refers to administration of one treatment modality before, during or after administration of the other treatment modality to the individual.

Unless clearly indicated otherwise, the term "individual" as used herein refers to a mammal, including but not limited to, bovine, horse, feline, rabbit, canine, rodent, or primate (e.g., human). In some embodiments, an individual is a human. In some embodiments, an individual is a non-human primate such as chimpanzees and other apes and monkey species. In some embodiments, an individual is a farm animal such as cattle, horses, sheep, goats and swine; pets such as rabbits, dogs and cats; laboratory animals including rodents, such as rats, mice, and guinea pigs; and the like. The invention may find use in both human medicine and in the veterinary context.

As used herein and in the appended claims, the singular forms "an," and "the" include plural reference unless the context clearly indicates otherwise.

It is understood that aspect and variations of the invention described herein include "consisting" and/or "consisting essentially of" aspects and variations.

Compounds

In one aspect, provided is a compound of the formula

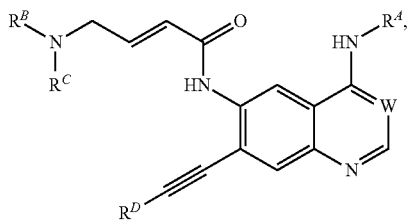
(I)

or a salt, solvate, or physiologically functional derivative thereof, wherein:

W is N or C—CN;

$R^A$ is a substituted aryl or substituted heteroaryl;

each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with 1 to 3 groups independently selected from the group consisting of oxo, halogen and —$OR^1$; or $R^B$ and $R^C$ are taken together with the nitrogen atom to which they are attached to form a 4 to 7-membered heterocyclyl, which is optionally substituted with up to 3 groups independently selected from the group consisting of halogen, oxo, —$OR^1$, —$NR^2R^3$, $C_1$-$C_3$ alkyl and $C_3$-$C_6$ cycloalkyl;

$R^D$ is a heterocyclyl containing 1-3 hetero ring atoms selected from "O", "N", S(O)", or "S(O)$_2$", where the heterocyclyl is optionally substituted with 1 to 3 groups independently selected from halogen, oxo, —$OCF_3$, —$CF_3$—$NR^2R^3$, $C_1$-$C_3$ alkyl and $C_3$-$C_6$ cycloalkyl; and each $R^1$, $R^2$ and $R^3$ is independently selected from H and $C_1$-$C_3$ alkyl.

In a compound of the formula (I), or a salt, solvate, or physiologically functional derivative thereof, $R^A$ is a substituted monocyclic, bicyclic or tricyclic aryl or a substituted monocyclic, bicyclic or tricyclic heteroaryl. In some embodiments, $R^A$ is a substituted monocyclic, bicyclic or tricyclic aryl. In some embodiments, $R^A$ is a substituted phenyl. In one variation, $R^A$ is phenyl substituted with 1 to 3 substituents independently selected from fluoro, chloro, bromo, ethynyl, benzenesulfonyl, optionally substituted $C_1$-$C_3$ alkyl (e.g., methyl), and —$OR^4$; where $R^4$ is optionally substituted $C_1$-$C_3$ alkyl (e.g., substituted methyl) or optionally substituted heteroaryl. In one variation, $R^A$ is phenyl substituted with 1 to 3 substituents independently selected from fluoro, chloro, bromo, ethynyl and methyl.

In one variation, $R^A$ is a substituted phenyl selected from the group consisting of

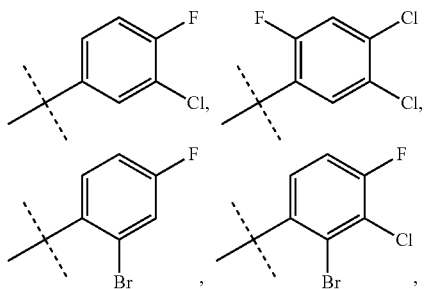

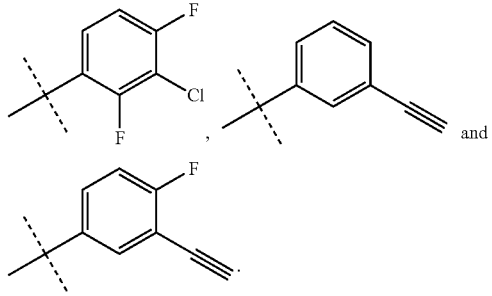

In one specific variation, $R^A$ is

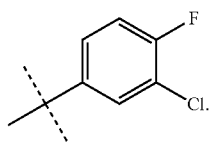

In another variation, $R^A$ is a substituted phenyl selected from the group consisting of

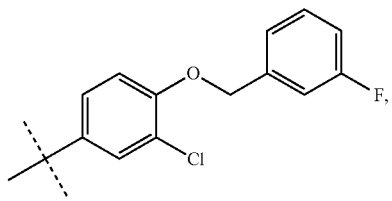

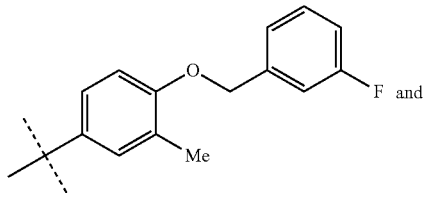

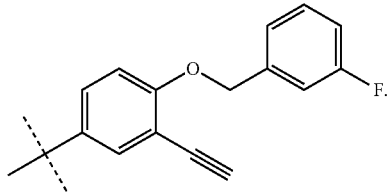

in another variation, $R^A$ is a substituted phenyl selected from the group consisting of

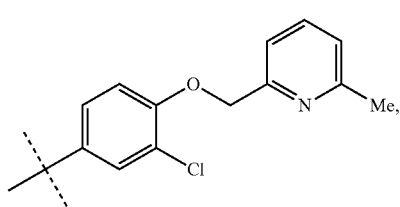

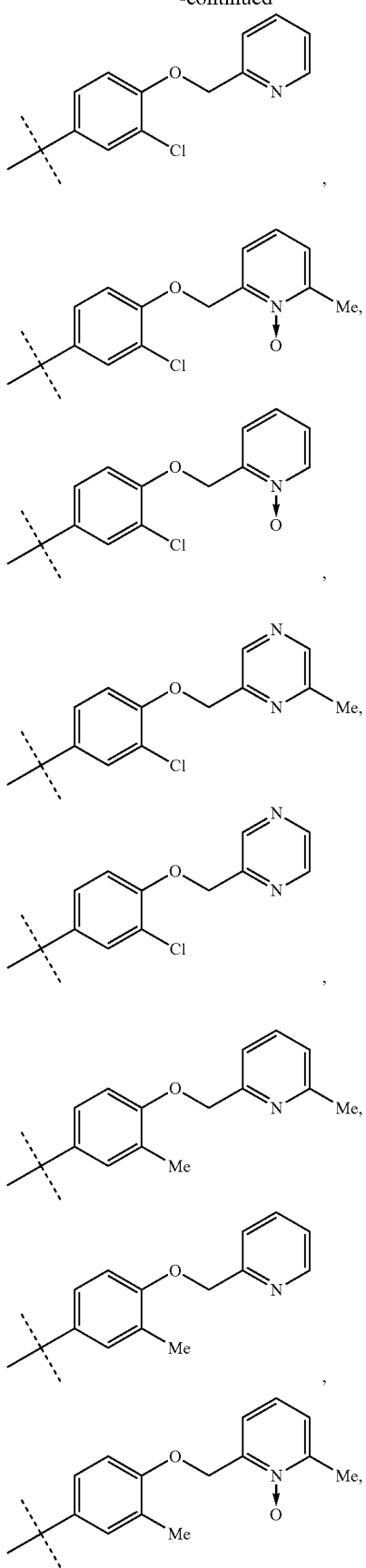
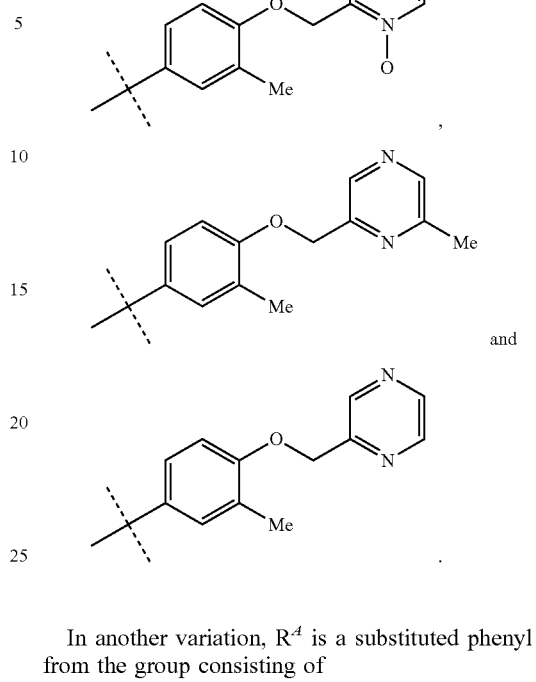
In another variation, $R^A$ is a substituted phenyl selected from the group consisting of
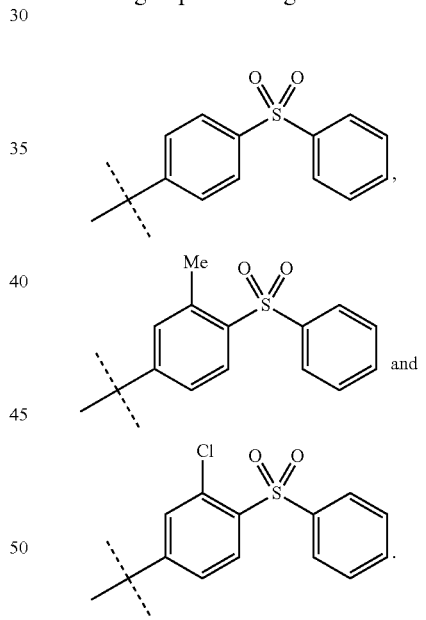
In another variation, $R^A$ is a substituted phenyl selected from the group consisting of
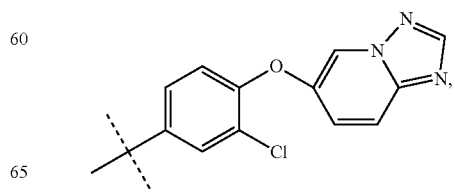

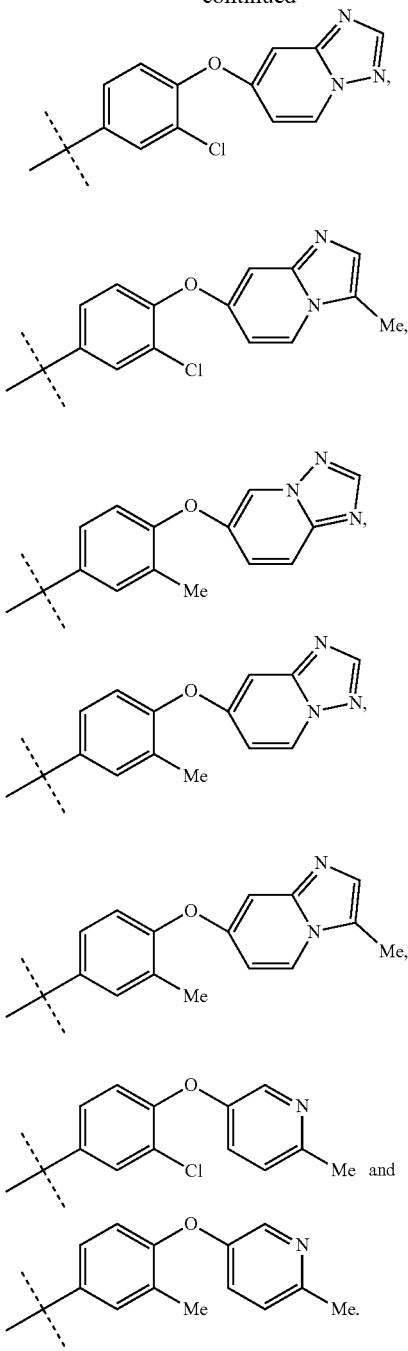

In some embodiments, $R^A$ is a substituted monocyclic, bicyclic or tricyclic heteroaryl. In one variation, $R^A$ is a substituted heteraryl selected from the group consisting of

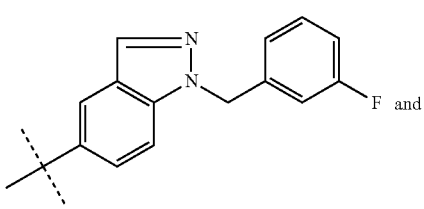

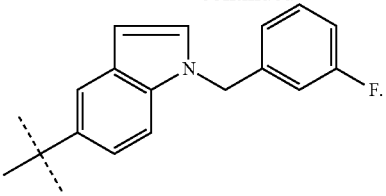

It is understood and clearly conveyed herein that each and every variation of $R^A$ described herein may be combined with each and every variation of other variables (e.g., $R^B$, $R^C$, $R^D$ and W) described herein, where applicable, as if each and every combination were listed separately.

In some embodiments, each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with up to three groups independently selected from the group consisting of oxo, halogen and —$OR^1$. In some embodiments, each $R^B$ and $R^C$ is independently H, $C_1$-$C_3$ alkyl or $C_3$-$C_6$ cycloalkyl. In some embodiments, each $R^B$ and $R^C$ is independently $C_1$-$C_3$ alkyl. In a specific embodiment, each $R^B$ and $R^C$ is methyl. In some embodiments, each $R^B$ and $R^C$ is independently H or $C_1$-$C_3$ alkyl optionally substituted with 1 to 3 groups independently selected from the group consisting of oxo, halogen and —$OR^1$. In some of these embodiments, $R^1$ is H. In some of these embodiments, $R^1$ is $C_1$-$C_3$ alkyl (e.g., methyl).

In some embodiments, $R^B$ and $R^C$ are taken together with the nitrogen atom to which they are attached to form a 4 to 7-membered heterocyclyl, which is optionally substituted with 1 to 3 groups independently selected from the group consisting of halogen, oxo, —$OR^1$, —$NR^2R^3$, $C_1$-$C_3$ alkyl and $C_3$-$C_6$ cycloalkyl, where each $R^1$, $R^2$ and $R^3$ is independently selected from H and $C_1$-$C_3$ alkyl.

In some embodiments, W is N. In some embodiments, W is C—CN.

In some embodiments, $R^D$ is a 4 to 10-membered heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl where each $R^1$, $R^2$ and $R^3$ is independently selected from H and $C_1$-$C_3$ alkyl. In some embodiments, $R^D$ is a 5 or 6-membered heterocyclyl containing 1 annular hetero atom (e.g., oxygen), optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl. In one variation, $R^D$ is a mono-cyclic heterocyclyl such as tetrahydrofuanyl (e.g., tetrahydrofuan-3-yl). In one variation, $R^D$ is a bicyclic heterocyclyl such as 3-oxabicyclo[3.1.0]hexyl (e.g., 3-oxabicyclo[3.1.0]hexan-6-yl and 3-oxabicyclo[3.1.0]hexan-1-yl).

It is understood and clearly conveyed herein that each and every variation of $R^D$ described herein may be combined with each and every variation of other variables (e.g., $R^A$, $R^B$, $R^C$ and W) described herein, where applicable, as if each and every combination were listed separately. For example, in one variation, provided is a compound of the formula (I), or salt, solvate, or physiologically functional derivative thereof, where W is N, $R^A$ is 3-chloro-4-fluorophenyl, each $R^B$ and $R^C$ is methyl, and $R^D$ is a tetrahydrofuan-3-yl, 3-oxabicyclo[3.1.0]hexan-6-yl or 3-oxabicyclo[3.1.0]hexan-1-yl. In a particular variation, $R^D$ is 3-oxabicyclo[3.1.0]hexan-6-yl.

In some embodiments, the compound is of the formula (I), or a salt, solvate, or physiologically functional derivative thereof, where W is N or a C—CN group; $R^A$ is a substituted monocyclic, bicyclic or tricyclic aryl or heteroaryl moiety; each $R^B$ and $R^C$ is independently selected from H, $C_1$-$C_3$ alkyl and $C_3$-$C_6$ cycloalkyl, where each of the above alkyl and cycloalkyl is optionally substituted with up to three groups independently selected from the group consisting of oxo, halogen and —$OR^1$; or $R^B$ and $R^C$ together with the atoms to which they are attached can form a 4 to 7-membered heterocyclyl ring, which is optionally substituted with up to 3 groups independently selected from halogen, oxo, —$OR^1$, —$NR^2R^3$, $C_1$-$C_3$ alkyl and $C_3$-$C_6$ cycloalkyl; $R^D$ is a mono, or bicyclic or spiro-cyclic 4 to 10-membered heterocyclyl group containing 1-3 hetero ring atoms selected from "O", "N", "S", S(O)", or "S(O)$_2$", whereas the heterocyclic ring is optionally substituted with up to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl; and $R^1$, $R^2$, and $R^3$ are independently selected from H and $C_1$-$C_3$ alkyl.

In a preferred embodiment, W is N.

In another preferred embodiment, $R^B$ and $R^C$ are independently $CH_3$.

Preferred examples of $R^A$ in the formula (I) include, but not limited to:

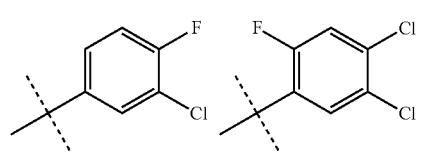

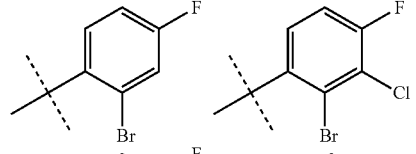

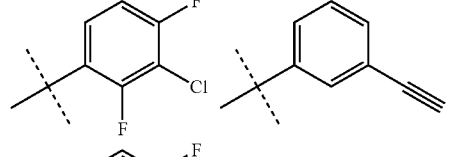

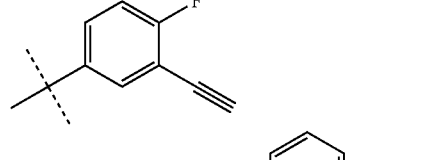

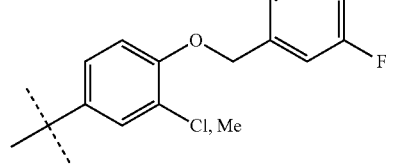

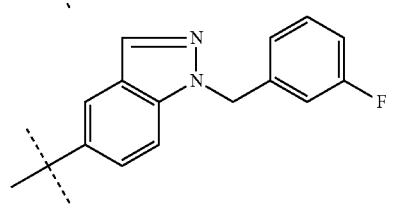

-continued

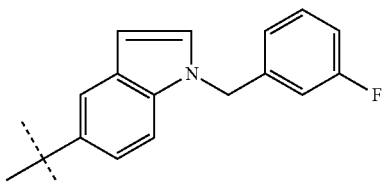

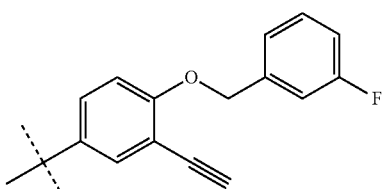

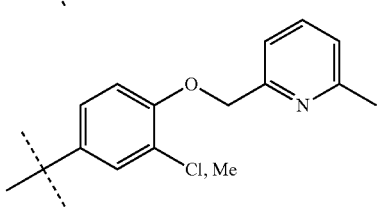

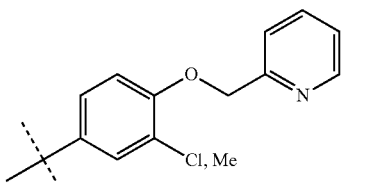

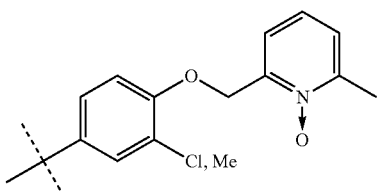

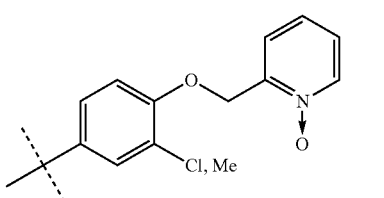

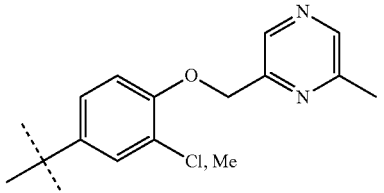

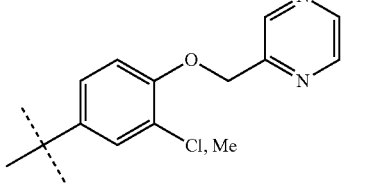

-continued

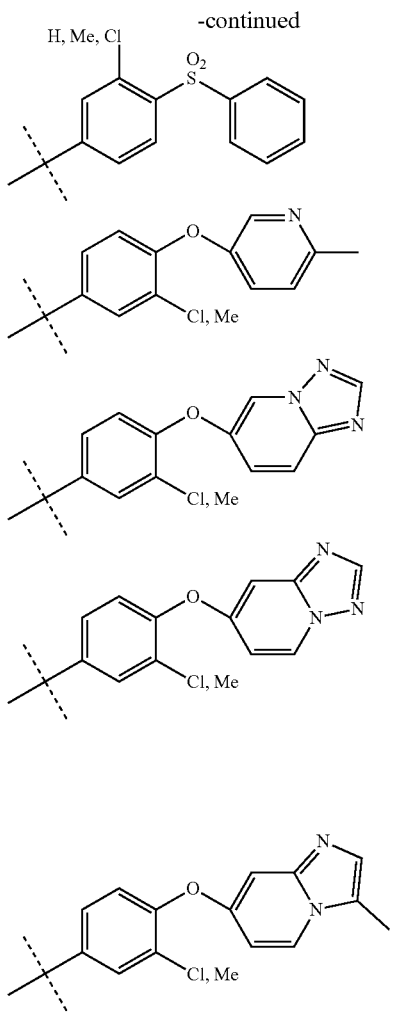

In some embodiments, provided is a compound selected from the group consisting of: (E)-N-(4-(3-chloro-4-fluorophenylamino)-7-(2-(tetrahydrofuran-3-yl)ethynyl)quinazolin-6-yl)-4-(dimethylamino)but-2-enamide, (E)-N-(4-(3-chloro-4-fluorophenylamino)-7-(2-((S)-tetrahydrofuran-2-yl)ethynyl)quinazolin-6-yl)-4-(dimethylamino)but-2-enamide, (E)-N-(4-(3-chloro 4-fluorophenylamino)-7-(2-((R)-tetrahydrofuran-2-yl)ethynyl)quinazolin-6-yl)-4-(dimethylamino)but-2-enamide, (E)-N-(4-(3-chloro-4-fluorophenylamino)-7-(2-((1R,5S,6s)-3-oxa-bicyclo[3.1.0]hexan-6-yl)ethynyl)quinazolin-6-yl)-4-(dimethylamino)but-2-enamide, (E)-N-(4-(3-chloro-4-fluorophenylamino)-7-(2-(3-oxa-bicyclo[3.1.0]hexan-1-yl)ethynyl)quinazolin-6-yl)-4-(dimethylamino)but-2-enamide, (E)-N-(4-(3-chloro-4-fluorophenylamino)-7-(2-(1R,5S)-3-oxa-bicyclo[3.1.0]hexan-1-yl)ethynyl)quinazolin-6-yl)-4-(dimethylamino)but-2-enamide and (E)-N-(4-(3-chloro-4-fluorophenylamino)-7-(2-((1S,5R)-3-oxa-bicyclo[3.1.0]hexan-1-yl)ethynyl)quinazolin-6-yl)-4-(dimethylamino)but-2-enamide; and salts, solvates and physiologically functional derivative thereof.

Compounds provided herein may possess one or more asymmetric centers, and such compounds can be produced as individual stereoisomers (e.g., an (R)- or (S)-enantiomer or a diastereomer) or as mixtures thereof. Unless indicated otherwise, the description or naming of a particular compound in the specification and claims is intended to include both individual enantiomers and mixtures, racemic or otherwise, thereof. Accordingly, this invention also includes racemates and resolved enantiomers, and diastereomers of compounds of the formula (I) or any variations detailed herein. The methods for the determination of stereochemistry and the separation of stereoisomers are well known in the art. See discussion in Chapter 4 of "March's Advanced Organic Chemistry", 6th ed. M. B. Smith and J. March, John Wiley and Sons, New York, (2007), incorporated herein by reference.

The present invention also includes isotopically-labeled compounds of the formula (I) or any variations detailed herein. The isotopically labeled compounds are identical to the compounds of this invention, but for the faction one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^2H$, $^3H$, $^{11}C$, $^{13}C$, $^{14}C$, $^{13}N$, $^{15}O$, $^{17}O$, $^{32}P$, $^{35}S$, $^{18}F$, $^{36}Cl$. Certain isotope labeled compounds (e.g. $^3H$ and $^{14}C$) are useful in compound or substrate tissue distribution study. Certain heavier isotope (e.g. $^2H$) may afford certain therapeutical advantage resulting from possible greater metabolic stability.

The invention also embraces solvates, pharmaceutically acceptable prodrugs, pharmaceutically active metabolites, and pharmaceutically acceptable salts of compounds of the formula (I) or any variations detailed herein.

The term "solvate" refers to an aggregate of a molecule with one or more solvent molecules, such as hydrate, alcoholate (aggregate or adduct with alcohol), and the like.

The term "physiologically functional derivative" used herein relates to any physiologically acceptable derivative of an inventive compound of the formula I, for example an ester which on administration to a mammal, for example humans, is capable of forming (directly or indirectly) a compound of the formula I or an active metabolite thereof.

The physiologically functional derivatives also include prodrugs of the compounds of the invention. Such prodrugs may be metabolized in vivo to a compound of the invention. These prodrugs may or may not be active themselves and are also an object of the present invention.

A "pharmaceutically acceptable prodrug" is a compound that may be converted under physiological conditions or by solvolysis to the specified compound or to a pharmaceutically acceptable salt of such compound.

A "pharmaceutically active metabolite" is a pharmacologically active product produced through metabolism in the body of a specified compound or salt thereof. Metabolites of a compound may be identified using routine techniques known in the art and their activities determined using tests such as those described herein.

Prodrugs and active metabolites of a compound may be identified using routine techniques known in the art. Various forms of prodrugs are known in the art. For examples of such prodrug, derivatives, see, for example, a) Design of Prodrugs edited by H. Bundgaard, (Elsevier, 1985) and Methods in Enzymology, Vol. 42, p. 309-396, edited by K. Widder, et al. (Academic Press, 1985); b) Chapter 27, "Recent Advances in Oral Prodrug Discovery", A. Cho in Annual Reports in Medicinal Chemistry, edited by A. Wood (Academic Press, 2006), 41:395. c) Prodrugs: Challenges and Rewards, Part 1 and 2, edited by V. J. Stella, et al. (Springer, 2007).

A "pharmaceutically acceptable salt" is a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable sale. Examples of pharmaceutically acceptable salts include those salts prepared by reaction of the compounds of the present invention with a mineral or organic acid or an inorganic base, such salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitromenzoates, hydroxybenzoates, methoxybenzoates, phthalates, sulfonates, xylenesulfonates, pheylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, tosylates, besylates, acetate and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alphahydroxy acid such as citric acid or tartaric acid an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

Also provided are salts of compounds referred to herein, such as pharmaceutically acceptable salts. The invention also includes any or all of the stereochemical forms, including any enantiomeric or diastereomeric forms, and any tautomers or other forms of the compounds described.

The compounds of the invention may also be present in various polymorphous forms, for example as amorphous and crystalline polymorphous forms. All polymorphous forms of the compounds of the invention are included within the scope of the invention and are another aspect of the invention.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

General Synthetic Methods

The inventive compounds may be prepared using the reaction routes and synthesis schemes as described herein, employing the techniques available in the art using starting materials that are readily available. For example, a compound of the formula (I), or a pharmaceutically acceptable salt thereof, may be prepared by any process known to be applicable to the preparation of chemically related compounds. Suitable processes include, for example, those illustrated in WO2007/054550, in Cha, M. Y.; Lee, K.-O., et al., *J. Med. Chem.* (2009), 52:6880-6888, and in Tsou, H.-R., Overbeek-Klumpers, E. G.; et al., *J. Med. Chem.* (2005), 48:1107-1131. Such processes, when used to prepare compounds of the formula (I) are provided as a further feature of the invention. Necessary starting materials may be obtained by standard procedures of synthetic organic chemistry. The preparation of such starting materials is described in conjunction with the following representative processes and within the accompanying Examples. Alternatively, the necessary starting materials can be obtained by analogous procedures to the illustrated, which are within the ordinary skill of an organic chemist.

The following synthetic schemes are meant to be representative examples only and are not mean to limit the invention in any way.

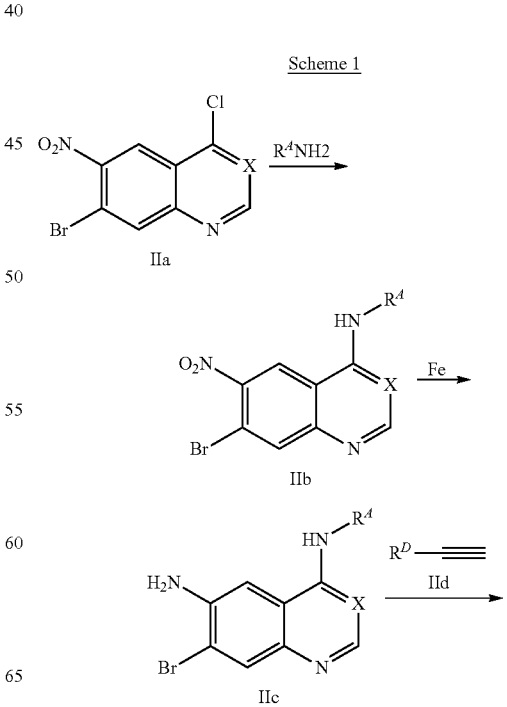

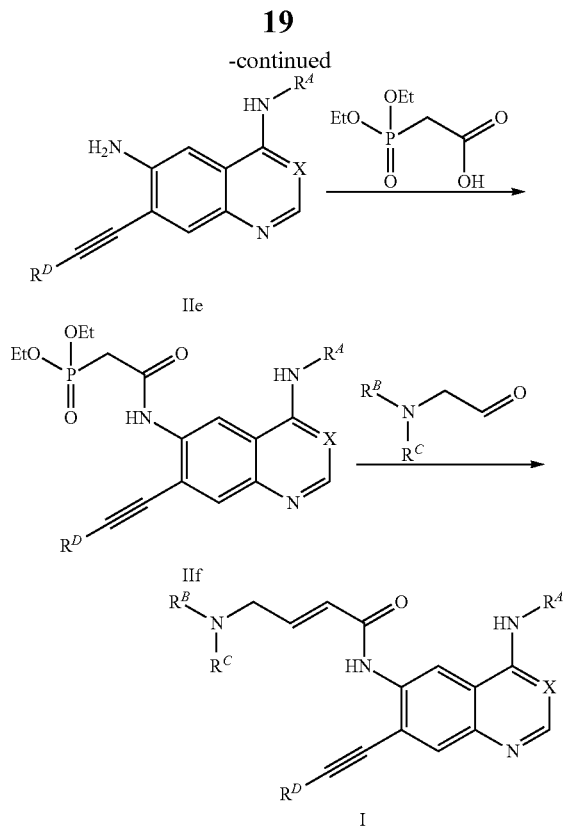

As shown in Scheme 1, aromatic nucleophilic substitution between the compound of Formula IIa (see Rewcastle, G. W., et al., J. Med. Chem (1996), 39:918-928.) and an amine $R^A NH_2$ affords a compound of Formula IIb. Aniline of Formula IIe may be obtained via the reduction of the nitro group with iron powder and acetic acid in aqueous ethanol. Alternatively, tin(II) chloride in acid or platinum on carbon can be used for the reduction. Sonagoshira reaction between an alkyne of Formula IId and a compound of Formula IIe is then carried with a palladium catalyst (such as $Pd(dppf)Cl_2$ or $Pd(PPh_3)_4$), copper(I) iodide and an alkylamine (such as triethylamine or butylamine) in an anhydrous aprotic solvent (such as THF or DMF) to give a compound of Formula IIe. Coupling of diethyiphosphonoacetic acid with a compound of Formula IIe is carried out with a usual amide formation method, such as carbodiimidazole (CDI) and 1-ethyl-3-(3-dimethyllaminopropyl)carbodiimide (EDC). The resulted compounds of Formula IIf can be further reacted with an appropriate 2-aminoacetaldehyde to give the final compounds of Formula I. (Dppf is 1,1'-Bis(diphenylphosphino) ferrocene, a his phosphine ligand to palladium.)

In another prospective, scheme 2 illustrated one of the general method for the preparation of alkynes of formula IId.

Scheme 2

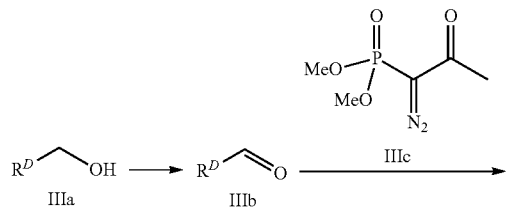

A primary alcohol of formula IIIa is oxidized to an aldehyde of Formula IIIb, with an oxidant such as PDC or PCC or Swern Oxidation. Further transformation of an aldehyde IIIb to an alkyne of Formula IId can be accomplished by the reaction with diazo compound IIIc (see Ohira, S. *Synth. Commun.* (1989), 19:561-564; and S. Mueller, S.; Liepold, B.; Roth, G. J.; Bestmann, J. *Synlett.* (1996), 521-22.)

Methods of Treatment

Compounds provided herein inhibit the activity of ErbB family receptor tyrosine kinases. Thus provided are methods of treating diseases or medical conditions mediated by type I receptor tyrosine kinases which comprises administering to an individual (e.g., a mammal) in need thereof an effective amount of a compound of the formula (I), or a pharmaceutically acceptable salt, solvate or in vivo transformable prodrug thereof. The type I receptor tyrosine kinase mediated condition that can be treated according to the methods of this invention includes hyperproliferative disorders, such as cancer of the head and neck, lung, breast, colon, ovary, bladder, stomach, kidney, skin, pancreas, blood (e.g., leukemias and lymphomas), esophagus, uterus or prostate, among other kinds of hyperproliferative disorders. In some embodiments, the cancer is head and neck cancer, lung cancer (e.g., NSCLC), breast cancer, colon cancer, ovarian cancer, bladder cancer, gastric cancer, kidney cancer, skin cancer, pancreatic cancer, leukemias, lymphomas, esophageal cancer, uterine cancer or prostate cancer. In some embodiments, the cancer is a breast cancer, gastric cancer or lung cancer. In some embodiments, treatable using a compound of the invention are eriotinib (Tarceva®) resistant cancers, such as erlotinib-resistant lung cancers (e.g., an erlotinib-resistant non-small cell lung cancer). In some embodiments, the individual has been diagnosed to have a hyperproliferative disorder such as a cancer detailed herein.

In one aspect, compounds provided herein penetrate the brain blood barrier and have brain bioavailability. Thus provided is a method for treating a brain tumor in an individual in need thereof comprising administering to the individual an effective amount of a compound of the formula (I), or a salt, solvate, or physiologically functional derivative thereof. The brain tumor may be a primary brain tumor such as gliomas e.g., recurrent malignant glioma), CNS lymphoma, craniopharyngioma, meningioma, astrocytoma, glioblastoma multiforme (GBM) and other cancers that originate in the brain or the central nerve systems. More common types of brain tumors are metastatic brain tumors (also referred to as lesions or brain metastatsis) that originate from other organs. There has been an increase in metastatic lesions as people are surviving primary cancers for longer periods of time. Provided is a method for treating or preventing a metastatic brain tumor comprising administering to the individual an effective amount of a compound of the formula (I), or salt, solvate, or physiologically functional derivative thereof. The method includes preventing or delaying the development of brain metastasis of cancers such as lung cancer, breast cancer, colon cancer, ovarian cancer, bladder cancer, gastric cancer, kidney cancer, skin cancer, pancreatic cancer, leukemias, lymphomas, esophageal cancer, uterine cancer and prostate cancer. In some embodiments, the individual has been diagnosed to have a brain tumor such as a primary brain tumor or a metastatic brain tumor.

Therapeutically effective amounts of the compounds of the invention may be used to treat diseases mediated by modulation or regulation of ErbB family kinases. An "effective amount" is intended to mean that amount of compound that, when administered to a mammal in need of such treatment, is sufficient to effect treatment for a disease mediated by the activity of one or more ErbB family kinases. Thus, for example, a therapeutically effective amount of a compound of the formula (I), or a salt, active metabolite or prodrug thereof, is a quantity sufficient to modulate, regulate, or inhibit the activity of one or more ErbB family kinases such that a disease condition which is mediated by that activity is reduced or alleviated. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of this invention, an effective dosage of drug, compound, or pharmaceutical composition is an amount sufficient to accomplish prophylactic or therapeutic treatment either directly or indirectly.

The amount of a given agent that will correspond to such an amount will vary depending upon factors such as the particular compound, disease condition and its severity, the identity (e.g., weight) of the mammal in need of treatment, but can nevertheless be routinely determined by one skilled in the art.

In order to use a compound of the formula (I), or a pharmaceutically acceptable salt or in vivo cleavable prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the formula (I), or a pharmaceutically acceptable salt or in vivo cleavable prodrug thereof, as defined hereinbefore in association with a pharmaceutically acceptable diluent or carrier.

The compounds of the invention are administered either singly or in combination to a mammal to treat hyperproliferative disease, such as various types of cancer, e.g., cancer of the colon, ovary, bladder, stomach, lung, uterus, and prostate. The compound may be administered via any acceptable route, e.g., intra venous, oral, intra muscular, via suppository, etc. The compounds can be formulated as oral dosage forms, e.g., tablets, capsules, liquid suspension, etc, as suppositories, or may be prepared as a liquid for injection, for example. The skilled practitioner can select the appropriate route and dosage amount for treatment of the specific hyperproliferative disease to be treated.

The compounds of the formula (I), or any variations detailed herein, may be used advantageously in combination with other known therapeutic agents. The compound of the invention having brain penetration may be used in conjunction with a therapeutic agent for treating a cancer which is not originated in brain to treat of prevent brain metastasis of the caner. For example, a compound of the formula (I), or any variations detailed herein, such as a compound of Examples 1 to 7 (e.g., Compound KU113), or a salt, solvate, or physiologically functional derivative thereof, may be used in combination with Herceptin for treating or preventing brain metastasis of breast cancer.

Formulations

The compositions of the invention may be in a form suitable for oral use (for example as tablets, lozenges, capsules, suspensions, emulsions, dispersible powders or granules, syrups or elixirs), for topical use (for example as creams, ointments, gels, or aqueous or oily solutions or suspensions), for inhalation (for example as a finely divided powder or a liquid aerosol), for administration by insufflation (for example as a finely divided powder) or for parenteral administration (for example as a sterile aqueous or oily solution for intravenous, subcutaneous, or intramuscular dosing or as a suppository for rectal dosing). For example, compositions intended for oral use may contain one or more coloring, sweetening, flavoring and/or preservative agents.

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or oil such as peanut oil, or olive oil.

Aqueous suspensions generally contain the active ingredient in finely powdered form together with one or more suspending agents, such as sodium carboxymethylcellulose, methylcellulose, hydroxypropylethylcellulose, sodium alginate, polyvinyl-pyrrolidone, gum tragacanth and gum acacia; dispersing or wetting, agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent, and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil such as liquid paraffin, or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient, which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable vehicle or diluent using conventional procedures well known in the art.

Compositions for administration by insufflation may be in the form of a finely divided powder containing particles of average diameter of, for example, 30 μm or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurized aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The amount of a compound of this invention that is combined with one or more excipients to produce a single dosage form will necessarily vary depending upon the host treated and the particular route of administration. For example, a formulation intended for oral administration to humans may contain, for example, from 0.5 mg to 5 g of active agent compounded with an appropriate and convenient amount of excipients, which may vary from about 5 to about 98 percent by weight of the total composition. Dosage unit forms will generally contain about 1 mg to about 500 mg of an active ingredient. For further information on routes of administration and dosage regimes, see: Ansel's Pharmaceutical Dosage Forms and Drug Delivery Systems, by Loyd V. Allen, Howard C. Ansel, Nicholas G. Popovich, Lippincott Williams & Wilkins, 2004.

The size of the dose for therapeutic or prophylactic purposes of a compound of Formula I will naturally vary according to the nature and severity of the conditions, the age and sex of the animal or patient and the route of administration, according to well known principles of medicine.

EXAMPLES

Example A

Synthesis of Intermediate A and Intermediate B

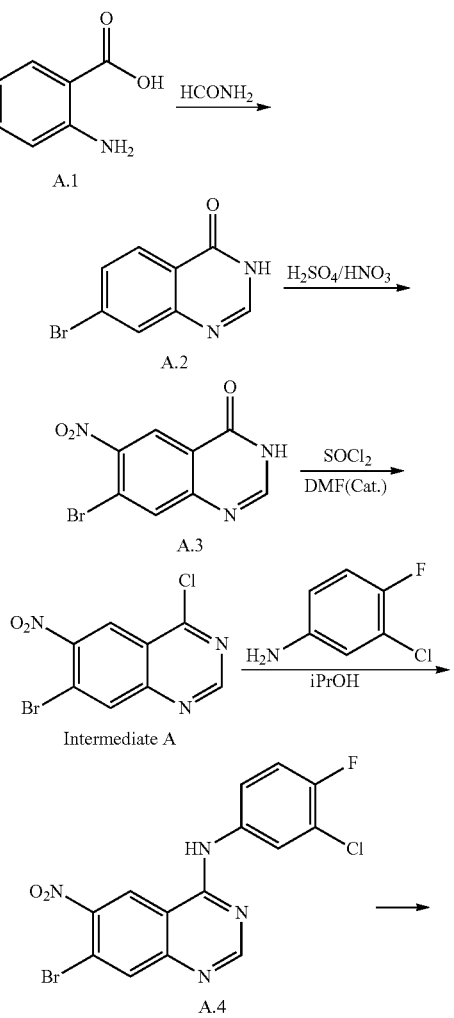

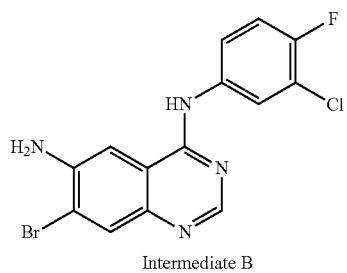

Intermediate B

7-Bromoquinazolin-4(3H)-one (compound A.1): 2-Amino-4-bromobenzoic acid (15.5 g) was dissolved in 100 mL of formamide and the solution was heated at 190° C. for 1.0h. After the reaction was cooled to room temperature, the solid was collected via filtration, rinsed with water, and dried to give 10.5 g of 7-bromo-4-quinazolinone, LCMS ESI(+) flak: 225/227 (M+1).

7-Bromo 6 nitroquinazolin-4(3H)-one (compound 4.2): A solution of 7-bromo-4-quinazolinone (2.6 g) in 5 mL of concentrated $H_2SO_4$ and 5 mL of fuming $HNO_3$ was heated at 100° C. for 1 h. After the reaction was cooled to room temperature, the mixture was poured into ice-water. The solid was collected via filtration, and used without further purification, 7-bronco-6-nitro-4-quinazolinone (mixed with 7-bromo-8-nitro-4-quinazolinone, LCMS ESI(+) fin/Z: 270/271 (M+1).

4-Chloro-7-bromo-6-nitroquinazoline (Intermediate A): A suspension of 7-bromo-6-nitro-4-quinazolinone (2.8 g) in 50 mL of $SOCl_2$ and 1 mL of DMF was heated at 100° C. until the formation of a homogenous solution. The reaction was concentrated under reduce pressure to afford intermediate A, 4-chloro-7-bromo-6-nitroquinazoline as a yellow solid (3.0 g, 91%, mixed with 4-chloro-7-bromo-8-nitroquinazoline), LCMS ESI(+) m/z: 270/271 (M+1, hydrolyzed back to compound A.2 during the LCMS run).

N-(3-chloro-4-fluorophenyl)-7-bromo-6-nitroquinazolin-4-amine (compound A.3): A mixture of intermediate A (2.88 g, 10 mmol) and 3-chloro-4-fluoroaniline (1.45 g, 10 mmol) in 50 mL of isopropanol was heated at 75° C. for 4 h. The mixture was cooled to room temperature and the solid was collected through filtration, rinsed with cold ethanol. Recrystallization of the solid with afforded pure N-(3-chloro 4 fluorophenyl)-7-bromo-6-nitroquinazolin-4-amine (2.03 g, 52%). LCMS ESI(+) m/z: 397/399/401 (M+1, isotope effect of Br and Cl).

7-Bromo-N4-(3-chloro-4-fluorophenyl)quinazoline-4,6-diamine (Intermediate B): Glacial acetic acid (3 mL) was added to a stirring solution of A.3 (588 mg, 1.47 mmol) in EtOH:H₂O (90 mL, 2:1 (v/v)), followed by reduced iron (328 mg, 5.87 mmol). The mixture was refluxed for 1 hr and cooled to room temperature. 5M NaOH was added to adjust the pH to 7-8, diluted with EtOAc (100 mL), stirred vigorously for 30 min, and filtered through celite. The black cake was washed with warm EtOAc (2×100 mL) and the filtrates concentrated. The residue was diluted in H₂O (100 mL), extracted with MeOH:DCM (2×100 mL, 1:9 (v/v)), the organic layer was washed with brine (100 dried over MgSO₄, and concentrated to a yellow green residue as intermediate B (1.21 g, high purity). LCMS ESI(±) m/z: 367/369/371 (M+1, isotope effect of Br and Cl).

Example 1

(E)-N-(4-chloro-4-fluorophenylamino)-7-(2-(tetrahydrofuran-3-yl)ethynyl)quinazolin-6-yl)-4-(dimethylamino)but-2-enamide

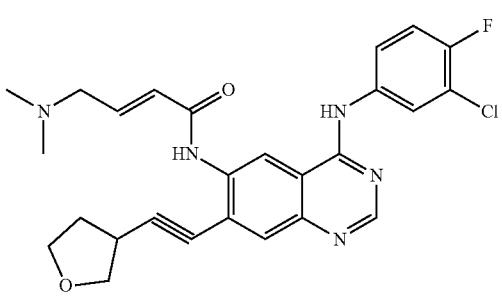 [SMILES: CN(C)C/C=C/C(=O)Nc1cc2c(Nc3ccc(F)c(Cl)c3)ncnc2cc1C#CC1CCOC1]

Scheme 1A

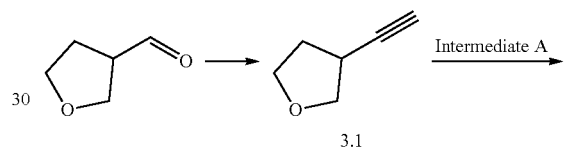

3.1

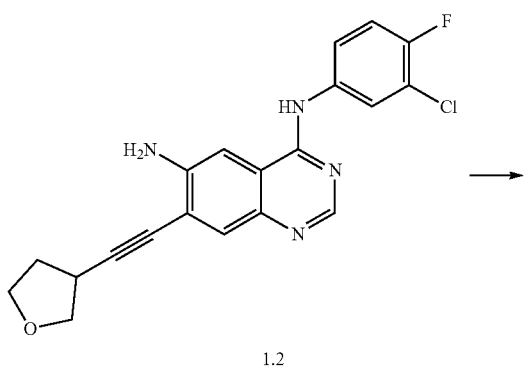

1.2

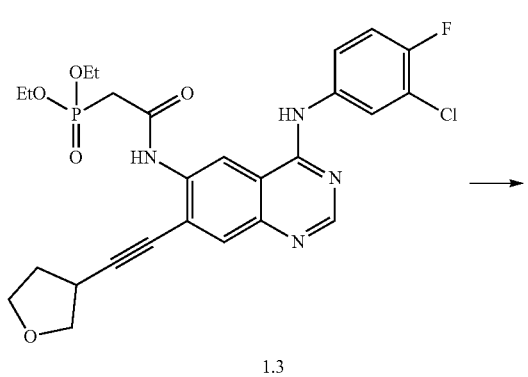

1.3

-continued

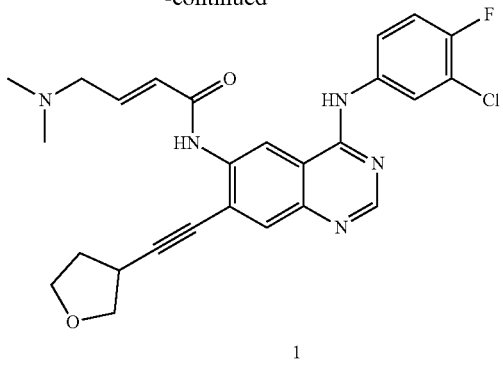

1

3-Ethynyl-tetrahydrofuran (Compound 1.1): To a stirred solution of Tetrahydrofuran-3-carboxaldehyde (extracted from commercially available 50% aqueous solution, 2.5 g, 25 mmol), $K_2CO_3$ (5 g), and MeOH (30 mL) was added Ohira-Bestmann reagent (5.0 g, 26 mmol) (reference: Ohira, S. *Synth. Commun.* 1989, 19, 561-4; and S. Muller, S.; Liepold, B.; Roth, G. J.; Bestmann, J. *Synlett* 1996, 521-22) at r.t. After 2 the solution was diluted with pentane/ether (1:1, 100 mL) and washed with $H_2O$ (50 mL, 2×) and sat. aq. NaCl (100 mL). The dried extract ($MgSO_4$) was concentrated in vacuo, keeping the bath temperature below 15° C., to about 5 mL of volume. This crude solution of compound 1.1 is used for next step.

N4-(3-chloro-4-fluorophenyl)-7-(2-(tetrahydrofuran-3-yl)ethynyl)quinazoline-4,6-diamine (compound 1.2): To the crude solution of compound 1.1 was added CuI (0.38 g, 0.20 mmol), Pd(dppf)Cl$_2$ (70 mg, 0.10 mmol), intermediate B (367 mg, 1.0 mmol), DMF (3 mL), and triethylamine (3 mL). The reaction was sealed and heated at 70° C. for 14 h. Reaction was then diluted with ethyl acetate (40 mL), filtered through a plug of silica (about 25 g), rinsed with ethyl acetate (50 mL). The filtrate was washed with ILO (50 mL, 2×) and sat. aq. NaCl (100 mL), dried with $MgSO_4$, filtered and concentrated. The residue was purified by column chromatography with 0-5% methanol in dichloromthane to give desired product 1.2 as light yellow solid (358 mg, 94%). LCMS (ESI)=383 (M+1).

Diethyl (4-(3-chloro-4-fluorophenylamino)-7-(2-(tetrahydrofuran-3-yl)ethynyl)quinazolin-6-ylcarbamoyl)methylphosphonate (compound 1.3): 1,1-Carbonyldiimidazole (CDI, 155 mg, 0.96 mmol) and diethylphosphonoacetic acid (188 mg, 0.96 myna) in THE (5 mL) were stirred at 40° C. for 30 min. A solution of 1.2 (344 mg, 0.90 mmol) in THE (3 mL) was added and the mixture stirred at 45° C. overnight. The reaction mixture was diluted in EtOAc (100 mL), washed with sat, $NaHCO_3$ (50 mL), FLO (100 mL), brine (100 mL), dried over $MgSO_4$, and concentrated. The gray solid was sonicated in ether (20 mL), filtered and dried in vacuo. The resulting off-white product 1.3 was used without further purification. LCMS (ESI) m/z=561 (M+1).

(E)-N-(4-(3-chloro-4-fluorophenylamino)-7-(2-(tetrahydrofuran-3-yl)ethynyl)quinazolin-6-yl)-4-(dimethylamino)but-2-enamide (Example 1): Lithium chloride monohydrate (105 mg, 1.28 mmol) was added to a solution of 1.3 (358 mg, 0.64 mmol) in EtOH (3 mL), followed by KOH (45% wt, 0.5 mL) at room temperature. After 5 min, a solution of dimethylaminoacetaldehyde-hydrogen sulphite adduct (214 mg, 1.28 mmol) in $H_2O$ (2 mL) was added, stirred for 2 h. Water (5 mL) was added to the reaction. After 15 min, solid was collected by filtration, and rinsed with water, and dried to afford Example 1 as a white solid (246 mg, 78%). $^1$HNMR (CDCl$_3$, 300 MHz) δ 9.16 (s, 1H), 8.66 (5, 1H), 8.25 (s, 1H), 7.98 (dd, 1H), 7.94 (s, 1H), 7.72 (s, 1H), 7.56 (m, 1H), 7.17 (t, 1H), 7.08 (dt, 1H), 6.24 (d, 1H), 4.10 (m, 2H), 3.97 (m, 2H), 3.41 (m, 1H), 3.21 (d, 2H), 2.44 (m, 1H), 2.35 (s, 6H), 2.23 (m, 1H), MS (ESI) m/z=494 (M+1).

Example 2

(E)-N-(4-(3-chloro-4-fluorophenylamino)-7-(2-((S)-tetrahydrofuran-2-yl)ethynyl)quinazolin-6-yl)-4-(dimethylamino)but-2-enamide

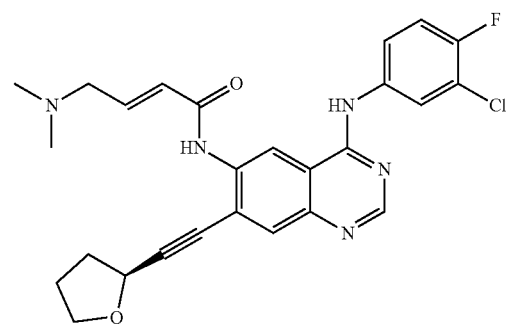 [SMILES: CN(C)C/C=C/C(=O)Nc1cc2c(Nc3ccc(F)c(Cl)c3)ncnc2cc1C#C[C@@H]1CCCO1]

Scheme 2A

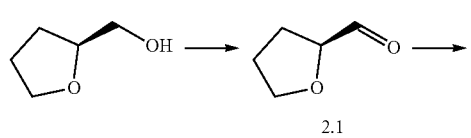

2.1

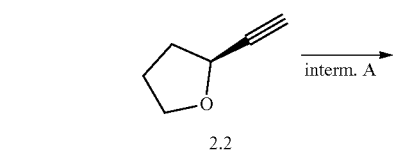

2.2

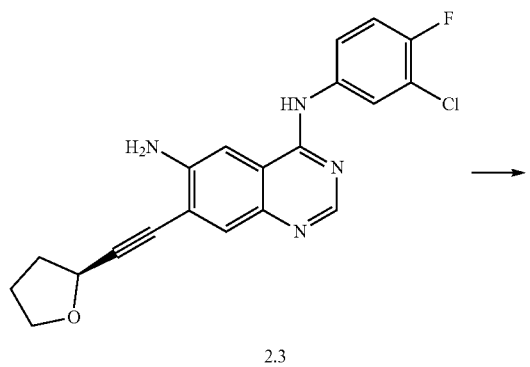

2.3

29

-continued

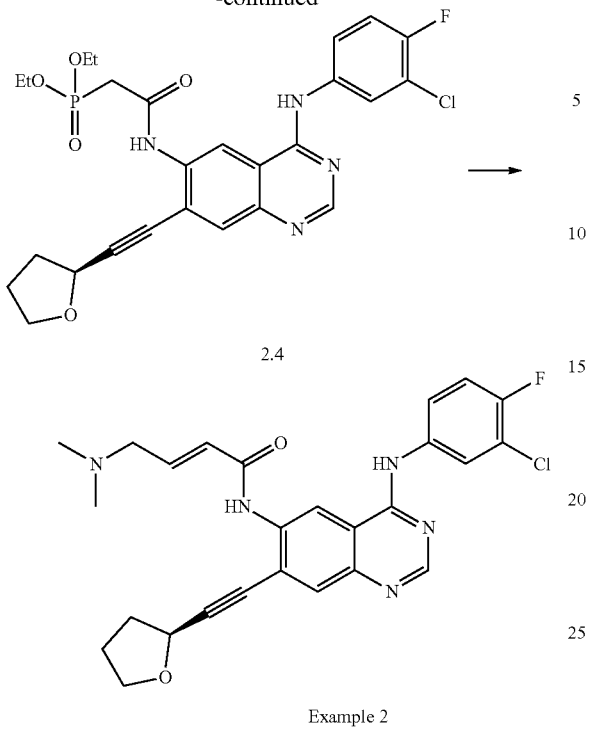

Example 2

(S)-Tetrahydrofuran-2-carboxaldehyde (compound 2.1): To a solution of ((S)-tetrahydrofuran-2-yl)methanol (1.02 g, 10 mmol) and molecule sieve 4 A, activated powder (5 g) in DCVI (40 mL) at 0° C. as added PCC (2.58 g, 12 mmol). Reaction was stirred at 0° C. for 2 h. To the stirring reaction mixture was added ether/pentane (1:1, 100 mL). The mixture was then filtered through Celite® (10 g), rinsed with ether. The residue was concentrated (water bath temperature <15° C.) to ~2 mL of volume.

(S)-2-Ethynyl-tetrahydrofuran (Compound 2.2): Crude compound 2.2 was prepared with the same procedure as the preparation of Compound Li, using (5)-tetrahydrofuran-2-carboxaldehyde (compound 2.1) instead of tetrahydrofuran-3-carboxaldehyde.

N4-(3-Chloro-4-fluorophenyl)-7-(2-((S)-tetrahydrofuran-2-yl)ethynyl)quinazoline-4,6-diamine (Compound 2.3): Compound 2.3 was prepared with the same procedure as the preparation of Compound 1.2, using (S)-2-ethynyl-tetrahydrofuran (Compound 2.2) instead of (S)-2-ethynyl-tetrahydrofuran (Compound 1.1). MS (ESI) m/z=383 (M+1).

Diethyl (4-(3-chloro-4-fluorophenylamino)-7-(2-((S)-tetrahydrofuran-2-yl)ethynyl)quinazolin-6-ylcarbamoyl)methylphosphonate (compound 2.4): Compound 2.4 was prepared with the same procedure as the preparation of Compound 1.3, using Compound 2.3 instead of Compound 1.2. MS (ESI) m/z=562 (M+1).

(E)-N-(4-(3-chloro-4-fluorophenylamino)-7-(2-((S)-tetrahydrofuran-2-yl)ethynyl)quinazolin-6-yl)-4-(dimethylamino)but-2-enamide (Example 2): Example 2 was prepared with the same procedure as the preparation of Example 1, using Compound 2.4 instead of 1.3. $^1$HNMR (CD$_3$OD, 300 MHz) δ 8.78 (s, 1H), 8.55 (s, 1H), 8.03 (s, 1H), 7.82 (s, 1H), 7.76 (m, 1H), 7.28 (m, 1H), 7.01 (m, 1H), 6.5 (m, 1H), 4.68 (m, 1H), 4.01 (m, 1H), 3.92 (m, 1H), 3.09 (m, 1H), 2.98 (s, 1H), 2.47 (s, 6H), 2.20 (m, 2H), 2.06 (m, 2H). MS (ESI) m/z=494 (M+1).

30

Example 3

(E)-N-(4-(3-chloro-4-fluorophenylamino)-7-(2-((R)-tetrahydrofuran-2-yl)ethynyl)quinazolin-6-yl)-4-(dimethylamino)but-2-enamide

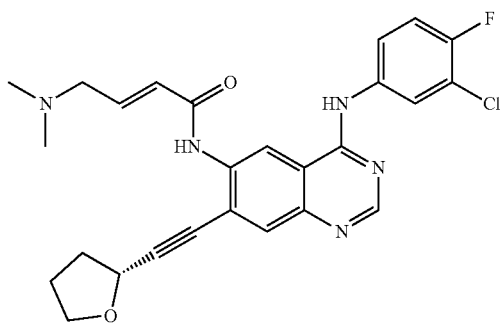 [SMILES: CN(C)C/C=C/C(=O)Nc1cc2c(Nc3ccc(F)c(Cl)c3)ncnc2cc1C#C[C@H]1CCCO1]

Example 3 was prepared with the same procedure as the preparation of Example 2, using (R)-tetrahydrofuran-2-methanol instead of (S)-tetrahydrofuran-2-methanol at the beginning of the synthesis. $^1$HNMR (CD$_3$OD, 300 MHz) δ 8.78 (s, 1H), 8.55 (s, 1H), 8.03 (s, 1H), 7.82 (s, 1H), 7.76 (m, 1H), 7.28 (m, 1H), 7.01 (m, 1H), 6.5 (m, 1H), 4.68 (m, 1H), 4.01 (m, 1H), 3.92 (m, 1H), 3.09 (m, 1H), 2.98 (s, 1H), 2.47 (s, 6H), 2.20 (m, 2H), 2.06 (m, 211). MS (ESI) m/z=494 (M+1).

Example 4

(E)-N-(4-(3-chloro-4-fluorophenylamino)-7-(2-((1R,5S,6s)-3-oxa-bicyclo[3.1.0]hexan-6-yl)ethynyl)quinazolin-6-yl)-4-(dimethylamino)but-2-enamide

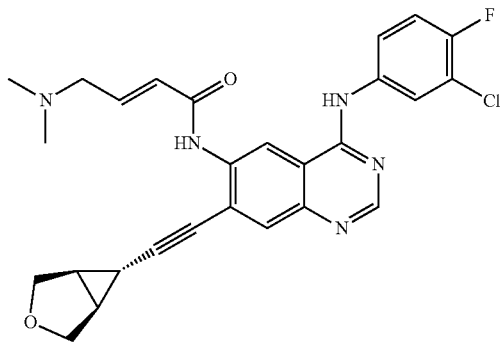 [SMILES: CN(C)C/C=C/C(=O)Nc1cc2c(Nc3ccc(F)c(Cl)c3)ncnc2cc1C#C[C@@H]1[C@H]2COC[C@@H]12]

Example 4 was prepared with the same procedures as the preparation of Example 2, using (3-oxa-bicyclo[3.1.0]hexan-6-yl)methanol. (reference for preparation: US2008/249087) instead of (S)-tetrahydrofuran-2-methanol at the beginning of the synthesis. $^1$HNMR (CDCl$_3$, 300 MHz) δ 9.10 (s, 1H), 8.69 (s, 1H), 8.24 (s, 1H), 8.00 (m, 1H), 7.91 (s, 1H), 7.87 (s, 1H), 7.56 (m, 1H), 7.15 (m, 3H), 6.23 (d, 1H), 4.05 (d, 1H), 3.81 (d, 1H), 3.23 (d, 1H), 2.36 (s, 4H), 2.19 (d, 1.65 (s, 6H). MS (ESI) m/z=506 (M+1).

Example 5

(E)-N-(4-(3-chloro-4-fluorophenylamino)-7-(2-(3-oxa-bicyclo[3.1.0]hexan-1-yl)ethynyl)quinazolin-6-yl)-4-(dimethylamino)but-2-enamide

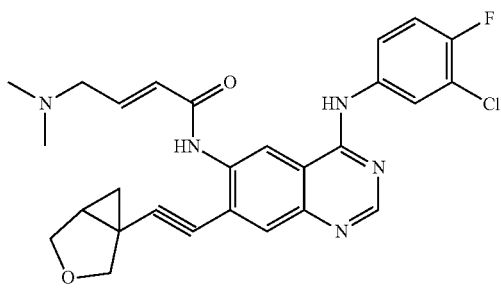 [SMILES: CN(C)C/C=C/C(=O)Nc1cc2c(Nc3ccc(F)c(Cl)c3)ncnc2cc1C#CC12COCC1C2]

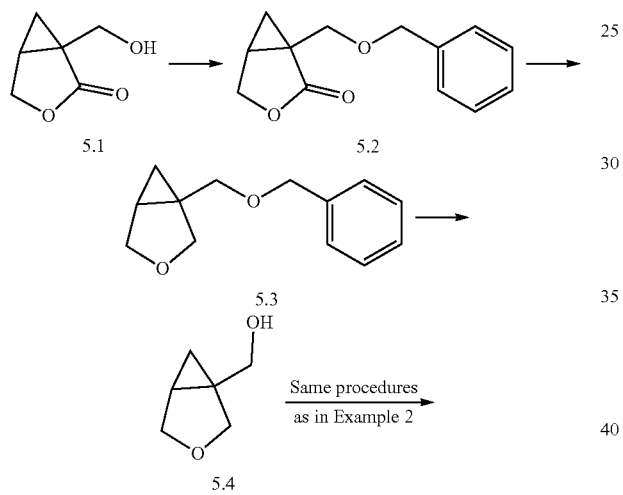

Example 5

1-((Benzyloxy)methyl)-3-oxa-bicyclo[3.1.0]hexan-2-one (compound 5.2): To a 0° C. solution of 1-(hydroxyethyl)-3-oxa-bicyclo[3.1.0]hexan-2-one (Compound 5.1, 12.8 g, 100 mmol) (preparation: Ostrowski, Tomasz; et al. Bioorganic & Medicinal Chemistry, 2006, 14 (10), p. 3535-3542) in THF (200 mL) was added sodium hydride (60% in mineral oil, 4.8 g) in 5 equal portions. After 10 min, benzyl bromide (20.5 g, 120 mmol) was added. Reaction was stirred at ambient temperature for 12 h, then cooled to 0° C. Saturated aqueous NH$_4$Cl solution (50 mL) is added to the reaction, and the mixture was partitioned between ether (300 mL) and water (50 mL). The organic layer was extracted with brine (50 mL), dried over MgSO$_4$, filtered and concentrated in vacuo. The residue is purified by column chromatography, eluting with 0-30% ethyl acetate in hexanes to give product 5.2 as colorless liquid (20.1 g, 92%). MS (ESI) m/z=219 (M+1).

1-((Benzyloxy)methyl)-3-oxa-bicyclo[3.1.0]hexane (Compound 5.3): The reference for this preparation: Sakai, N., et al. Synthesis, 2008 p. 3533-3536. To a solution of compound 5.2 (10.9 g, 50 mmol), indium bromide (InBr$_3$, 0.35 g) in chroloform (200 mL) was added triethylsilane (23.2 g, 200 mmol). The reaction mixture was heated at 65° C. for 16 h. The reaction mixture was cooled to room temperature, and concentrated. The residue was then purified by column chromatography, eluting with 0-20% ethyl acetate in hexanes to give product 5.3 as colorless liquid (8.9 g, 87%). MS (ESI) m/z=205 (1M+1).

3-Oxa-bicyclo[3.1.0]hexan-1-yl)methanol (Compound 5.4): A mixture of compound 5.3 (4.1 g, 20 mmol) and Pd—C(5%, 500 mg) in methanol was flushed with hydrogen, and then stirred under hydrogen balloon for 4 h. The reaction mixture was filtered through Celite®, rinsed with ether, and carefully concentrated (volatile product) to give the desired product 5.4, which is used without further purification.

(E)-N-(4-(3-Chloro-4-fluorophenylamino)-7-(2-(3-oxa-bicyclo[3.1.0]hexan-1-yl)ethynyl)quinazolin-6-yl)-4-(dimethylamino)but-2-enamide (Example 5): Example 5 was prepared with the same procedures as the preparation of Example 2, using 3-oxa-bicyclo[3.1.0]hexan-1-yl)methanol (Compound 5.4) instead of (S)-tetrahydrofuran-2-methanol. $^1$HNMR (DMSO-d$_6$, 300 MHz) δ 9.96 (s, 1H), 9.86 (s, 1H), 8.68 (s, 1H), 8.57 (s, 1H), 8.13 (dd, 1H), 7.99 (m, 2H), 7.43 (t, 1H), 6.80 (tt, 1H), 6.41 (d, 1H), 3.89 (d, 1H), 3.76 (s, 2H), 3.70 (d, 1H), 3.09 (d, 1H), 2.19 (s, 6H), 1.21 (m, 4H), 0.95 (m, 1H), MS (ESI) m/z=506 (M+1).

Example 6

(E)-N-(4-(3-chloro-4-fluorophenylamino)-7-(2-((1R,5S)-3-oxa-bicyclo[3.1.0]hexan-1-yl)ethynyl)quinazolin-6-yl)-4-(dimethylamino)but-2-enamide

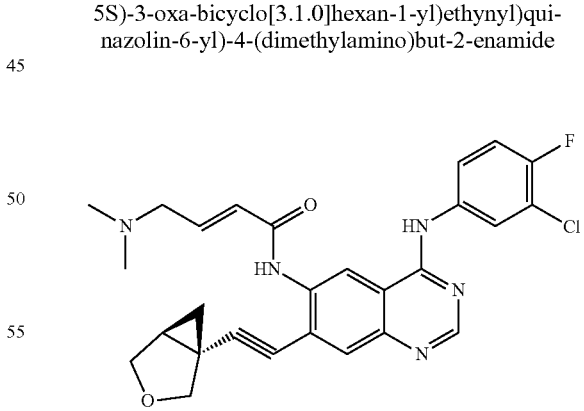

Example 6 was prepared with the same procedures as the preparation of Example 5, using (1R)-1-(hydroxymethyl) 3 oxa bicyclo[3.1.0]hexan-2-one (preparation: Moon, H. R.; et al., *Nucleosides, Nucleotides and Nucleic Acids* (2007), 26:975-978) instead of 1-(hydroxymethyl)-3-oxa-bicyclo [3.1.0]hexan-2-one (Compound 5.1). $^1$HNMR (DMSO-d$_6$, 300 MHz) δ 9.96 (s, 1H), 9.86 (s, 1H), 8.68 (s, 1H), 8.57 (s, 1H), 8.13 (dd, 1H), 7.99 (m, 2H), 7.43 (t, 1H), 6.80 (tt, 1H), 6.41 (d, 1H), 3.89 (d, 1H), 3.76 (s, 2H), 3.70 (d, 1H), 3.09 (d, 1H), 2.19 (s, 6H), 1.21 (m, 4H), 0.95 (m, 1H). MS (ESI) m/z=506 (M+1).

Example 7

(E)-N-(4-(3-chloro-4-fluorophenylamino)-7-(2-((1S, 5R)-3-oxa-bicyclo[3.1.0]hexan-1-yl)ethynyl)quinazolin-6-yl)-4-(dimethylamino)but-2-enamide

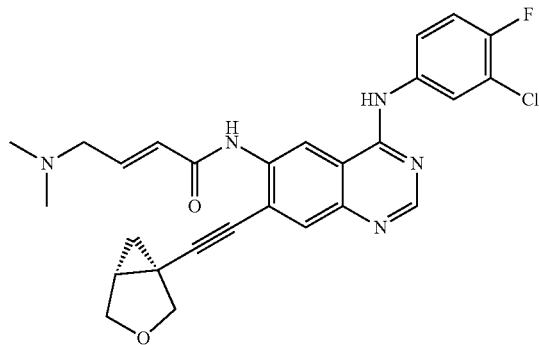 [SMILES: CN(C)C/C=C/C(=O)Nc1cc2c(Nc3ccc(F)c(Cl)c3)ncnc2cc1C#C[C@@]12COC[C@@H]1C2]

Example 7 was prepared with the same procedures as the preparation of Example 5, using (1S)-1-(hydroxymethyl)-3-coxa-bicyclo[3.1.0]hexan-2-one (preparation: Moon, H. R.; et al., *Nucleosides, Nucleotides and Nucleic Acids* (2007), 26:975-978) instead of 1-(hydroxymethyl)-3-oxa-bicyclo [3.1.0]hexan-2-one (Compound 5.1). $^1$HNMR (CD$_3$OD, 300 MHz) δ 8.85 (s, 1H), 8.53 (s, 1H), 8.05 (s, 1H), 7.80 (s, 1H), 7.75 (m, 1H), 7.25 (m, 1H), 7.0 (m, 2H), 6.60 (d, 1H), 6.40 (d, 1H), 3.95 (d, 1H), 3.86 (m, 1H), 3.58 (m, 2H), 3.21 (n, 2H), 2.34 (s, 6H), 1.20 (m, 1H), 1.1 (m, 1H), 0.95 (n, 1H), LCMS (ESI) m/z=506 (M+1).

Example 8

Kinase Assay for EGFR

The extent to which the compounds of the present invention modulate EGFR kinase activity can be determined using time-resolved Fret (TR-FRET) assay (LanthaScreen® kinase activity assay, from InVitrogen). The assay employs EGFR kinase (PV3872, Invitrogen), Tb-Py20 antibody (PV3552, InVitrogen) and fluorescein-poly GT (PV3610, InVitrogen).

The assay is performed in a Black 384-well plate (available from Corning). EGFR kinase (is diluted in TR-FRET Dilution Buffer (PV3189, InVitrogen) at concentration of 0.4 ug/ml as stock solution, and then 2-fold serial diluted. Addition of 1 mM ATP initiated the reaction, and the reaction is incubated for 1l1 reaction at room temperature. 10 μL of the Tb-antibody (from InVitrogen)+EDTA (from InVitrogen) solution prepared was added to each well of the assay plate and mix briefly, and incubated for 30 min. The signal is monitored by using M5 microplate reader (Ex=332 nm, Em=488 nm and 518 nm). Each compound is tested in duplicate wells. EGFR without compound is used as control. Staurosporine (available from Sigma) is used as positive control compound. Inhibition was calculated as percentage of the EGFR activity (without compound). Each compound in Examples 1 to 7 showed >50% inhibition at 100 nM.

Example 9

Kinase Assay for ErbB2

The assay is performed similarly to the kinase assay for ErbB2 as described above, except ErbB2 kinase protein is used instead of EGFR kinase protein. Each compound in Examples 1 to 7 showed >50% inhibition at 100 nM.

Example 10

Cell Proliferation Inhibition Assay for BT474

Human breast cancer BT474 cells was cultured in low glucose DMEM (Life Technologies 12320-032) containing 10% fetal bovine serum (FBS) at 37° C. in a humidified 10% CO2, 90% air incubator. Cells were harvested using trypsin EDTA, counted using a haemocytometer, and plated 10000 cell/well in a 96-well clear tissue culture plate. The cells were incubated for 24 h at 37° C. to allow adherence. A serials of concentrations of each compound (ranging from 30 um to 0.16 nM, 5-fold dilution) in 96-well plate, and incubated for 72h. Each concentration was tested in triplicate wells. During the cell proliferation assay, BT474 cells were cultured in low-glucose DMEM containing 5% FBS, 50 ug/ml gentamicin, and 0.3% v/v DMSO. The culture medium was removed via aspiration, and the cell viability was detected by using CCK-8 cell proliferation kit. The IC$_{50}$ value measured for each compound in Examples 1 to 7 is <100 nM.

Example 11

Anti-Proliferation Assay of NCI-N87 Cells

The anti-proliferative assays were performed in triplicates. 3000 cell/well of N87 cells were seeded in 96-well plate, and the cells were incubated for 24h at 37° C. to allow adherence. For the cell proliferation assay, N87 cells were cultured in full cell culture medium containing 0.3% v/v DMSO. A serials concentration of the tested compound (concentration range: 30 uM to 0.16 nM, 5-fold dilution) were added to the 96-welt plate. The incubation was continued for 72h. The culture medium was then removed, and the cell viability was measured by using CCK-8 cell proliferation kit as described in manual provided by the manufacturer. The log of the fractional growth inhibition was plotted against the log of the drug concentration, and the IC$_{50}$ values were interpolated from the resulting linear regression curve fit. The IC$_{50}$ value measured for Compound NT113 is <100 nM.

Example 12

Anti-Proliferation Assay of NCI-H1975 Cells

The anti-proliferative assays were performed in triplicates. 3000 cell/well of N1975 cells were seeded in 96-well plate (medium: RPMI 1640, 5% FBS. 2 mM L-Glutamine). After 24 h, removal the medium in the plate was followed by the addition of compound of serial dilution in medium to the wells. After 3 days, the cells were treated with CCK-8 kit and incubated for additional 4 hours at 37° C. The plate was read at 450 nm. The log of the fractional growth inhibition was plotted against the log of the drug concentration, and the IC$_{50}$ values were interpolated from the resulting linear regression curve fit. The IC$_{50}$ value measured for Compound NT113 is <1000 nM.

The biological activities of EGER and ErbB2 (HER2) kinase inhibition, and BT474, NCI-N87 and NCI-1-H1975 cell proliferation inhibition are listed in Table 1.

TABLE 1

| Example No. | Kinase inhibition IC$_{50}$ (nM) | | Cell Proliferation Inhibition IC$_{50}$ (nM) | | |
|---|---|---|---|---|---|
| | EGFR | ErbB2 | BT474 | NCI-N87 | NCI-H1975 |
| 1 | ++ | ++ | ++ | | |
| 2 | ++ | ++ | ++ | | |
| 3 | ++ | ++ | ++ | | |
| 4 | ++ | ++ | ++ | ++ | + |
| 5 | ++ | ++ | ++ | | |
| 6 | ++ | ++ | ++ | | |
| 7 | ++ | ++ | ++ | | |

Symbol: "++" indicates >50% inhibition at 100 nM, or IC50 < 100 nM; "+" indicates between 20% to 50% inhibition at 100 nM, or IC$_{50}$ between 100 and 1000 nM.

Example 13

In Vivo Efficacy in NCI-N87 Xenograft Mouse Model

NCI-N87 cell line was purchased from ATCC (American Type Culture Collection) and was cultured in RPMI1640+10% FBS+1% P/S antibiotics.

Male Balb/c nude mice, 6-8 week, 18±2 g (supplier: Shanghai SLAC Laboratory Animal Co. Ltd.) were used for the experiment. The purchased mice were adapted to the environment for 7 days before use, and were housed at 22-25° C. with humidity 40-70%, and light cycle with fluorescent light for 12-hour light (8:00-20:00) 12-hour dark. The mice have free access to food and water.

The cancer cells (NCI-N87) were implanted subcutaneous into the nude mice (right flank) with $5.0 \times 10^6$ cells in 0.1 ml PBS (50 mice). When the tumor size reaches a volume of 200 (150-200) mm$^3$, the tumor-bearing nude mice were randomly assigned into groups (10 mice/group), one group was served as vehicle, one group was administrated with Lapatinib ditosylate monohydrate (80 mg/kg, free base of Lapatinib, not salt, p.o. hid). The other two groups were administrated with NT113 (also referred to as KID 113) ((15 and 30 mg/kg, p.o.q.d, respectively). The administration period lasted for 4 weeks.

The mice were monitored twice daily for appearance and behavior, and for signs of morbidity and/or mortality. The tumor volume was measured twice a week, and the body weight was measured immediately before measuring the tumor volume throughout the whole study.

At end of the experiment (compound administration for four weeks), all the tumor-bearing mice were sacrificed by cervical dislocation under deep anesthesia. The tumor mass was resected, and weighed.

Tumor sizes were measured twice weekly in two dimensions using a caliper, and the volume was expressed in mm$^3$ using the formula: $V = \frac{1}{2} \times a \times b^2$ where a and b are the long and short diameters of the tumor, respectively. The tumor mass was weighed at the end of the experiment after harvested.

$V = \frac{1}{2} \times a \times b^2$ (a, h is maximum and minimum diameters respectively).

RTV (Relative Tumor Volume)=Vt/Vo

Vo is the tumor volume when the test article is initial administrated

Vt is the tumor volume of every measurement day after test article administration

T/C (%)=TRTV/CRTV×100%

TRTV: RTV of test article-treatment group; CRTV: RTV of control group Inhibition rate (%)=(average tumor volume of control group average cancer volume of test article treatment group)/average tumor volume of control group×100%

The tumor-bearing mice were treated for 4 weeks with different doses of KU (15 mg/kg, 30 mg/kg, pc), qd) and Lapatinib KUA-1, 80 mg/kg, p.o., bid, 7 days/week. At the day-7 after treatment, the RTV TIC KU113 (15 mg/kg, 30 mg/kg) groups were <30%, and the tumor growth inhibition was >70%. but the RTV TIC was 31% and tumor growth inhibition rat was 69% in the lapatinib group. The same result was observed as well when it comes to the tumor weight. On day 28 after treatment, all the tumor-bearing mice were sacrificed, and all the tumor masses were harvested to weigh.

Lapatinib (KUA-1, GlaxoSmithKline), a small-molecule kinase inhibitor of EGFR and ErbB2, led to a tumor inhibition rate of 92.9% on day 28 (the last day of the study).

KU113 treatment with 30 mg/kg, p.o., qd, 7 days/week led to body weight loss in the NCI-N87 xenograft tumor model. The body weight started to decrease in KU113-treated on the day 3 after dosing in the 30 mg/kg, p.o., qd, 7 days/week, and continued to decrease until reached the maximal body weight loss on day 11. The administration of the high dose (30 mg/kg) KU113 was stopped and never resumed. The body weight recovered to normal by day 28. The 15 mg/kg, po, qd dosing group was continued without predefined side effect. See FIG. 1.

As used herein, the term "po", "p.o." or "PO", used in combination with the term "qd" or "q.d.", means oral administration, once a day.

Example 14

In Vivo Efficacy in NCI-H1975 Xenograft Mouse Model

H1975 cells were purchased from ATCC were cultured in RPMI1640±10% FBS-1% P/S antibiotics. Balb/c nude mice, female, 6-8 week, 18+2 g were purchased from. Shanghai Laboratory Animal Co. Ltd. The purchased mice were adapted to the environment for 7 days before use, and were housed at 22-25° C. with humidity 40-70%, and light cycle with fluorescent light for 12-hour light (8:00-20:00) 12-hour dark.

Formulation: Erlotinib, afatinib (BIBW2992), and KU113 were dissolved in 2% DMA and 98% (40% HP-β-CD deionized water).

The cancer cells (H1975) were amplified and implanted into the nude mice (right flank) with $5.0 \times 10^6$ cells in PBS and 1:1 with matrigel in a total volume of 0.1 ml/mouse. When the tumor reaches a volume of 200 (150-200) mm$^3$, the tumor-bearing nude mice derived from H1975 cells were randomly assigned into several groups (10 mice/group), Group 1 served as vehicle; Groups 2 to 5 were administrated with afatinib at 20 mg/kg (p.o.q.d.), Compound KU113 at 10 mg/kg (po, qd); Compound KU113 at 20 mg/kg (po, qd) and erlotinib at 100 mg/kg (free base, p.o.q.d.); respectively. The animals were sacrificed after 4 weeks.

The mice were monitored twice daily for appearance and behavior, and for signs of morbidity and/or mortality. The tumor volume was measured twice a week, and the body weight was measured immediately before measuring the tumor volume throughout the whole study.

At end of the experiment (compound administration for four weeks)), all the tumor-bearing mice were sacrificed by cervical dislocation under deep anesthesia. The tumor mass was resected, and weighed.

Tumor sizes were measured twice weekly in two dimensions using a caliper, and the volume was expressed in mm$^3$ using the formula: V=½×a×b$^2$ where a and b are the long and short diameters of the tumor, respectively. The tumor mass was weighed at the end of the experiment after harvested.

V=½×a×b$^2$ (a, b is maximum and minimum diameters respectively).

RTV (Relative Tumor Volume)=Vt/Vo

Vo is the tumor volume when the test article is initial administrated

Vt is the tumor volume of every measurement day after test article administration

T/C (%)=TRTV/CRTV×100%

TRTV: RTV of test article-treatment group; CRTV: RTV of control group Inhibition rate (%)=(average tumor volume of control group average cancer volume of test article treatment group)/average tumor volume of control group×100%

Significant effective: T/C %<40%, P<0.05

Non-significant effective: T/C %>40%.

Figure 2:
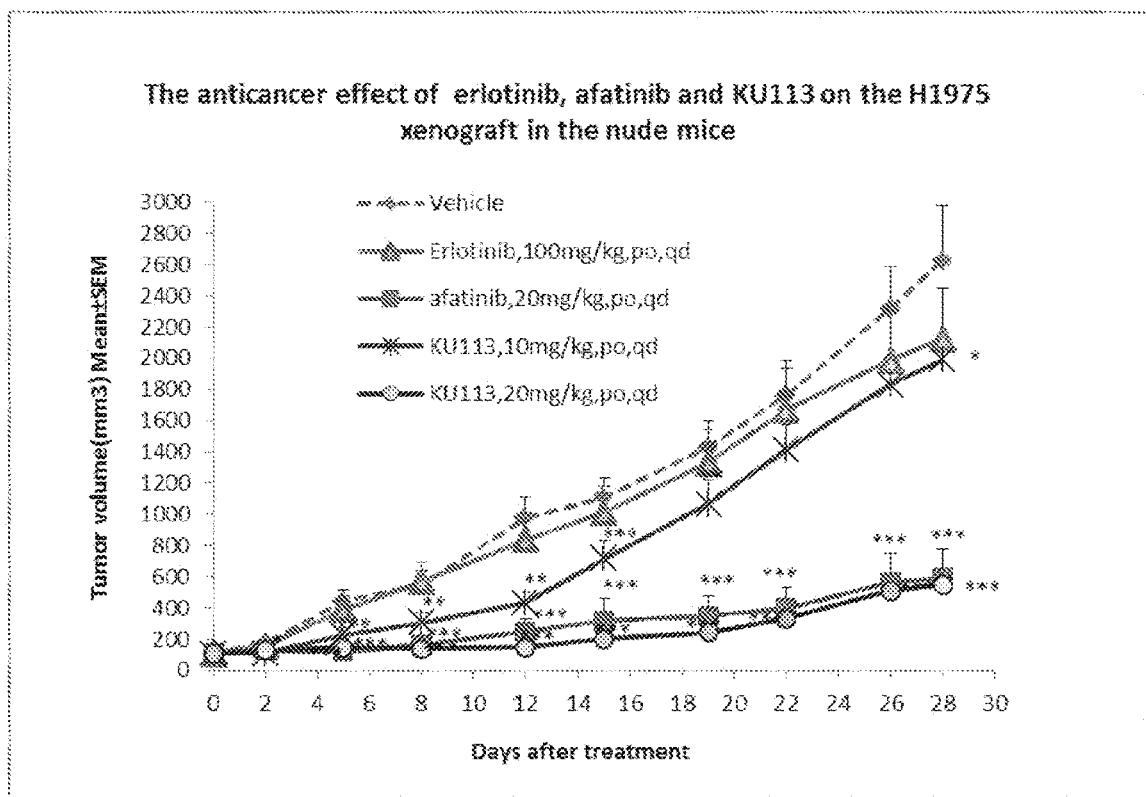
FIG. 2 shows the anticancer effect of Compound KU113 on the H1975 xenograft in the nude mice in comparison with erlotinib and afatinib.

As shown in FIG. 2, Compound KU113 in this model is significantly more effective than erlotinib; and comparable with afatinib.

Example 15

Intracranial Brain Tumor Xenograft Study

Tumor Cell Preparation.

Cells for human brain tumor xenografts are sourced either from tumors propagated as subcutaneous growths in athymic mice, or from cell culture. To prepare cells from subcutaneous tumors for transfer to the intracranial compartment, excised flank tumors are placed in culture dishes, where the tissue is initially minced with a scalpel and then mechanically disrupted by repetitive pipetting to create a cell aggregate suspension. The cell aggregate suspension is then passed through a 70 μM nylon mesh filter to produce a single cell suspension. The cell suspension is centrifuged at 1000 rpm for 10 minutes at 4° C., and the supernatant aspirated before resuspending the cell pellet in an appropriate volume of serum-free media to obtain a final working concentration. For preparing established cell lines for intracranial implantation, cells are harvested by trypsinizing monolayers, or by collecting neurosphere suspension cultures, then centrifuging and resuspending the cells as indicated above. The number of cells injected is variable dependent on neuroanatomical location of injection. For supratentorial injections, 3-5×10$^5$ cells in 3 μL of serum-free media (DMEM), whereas for brainstem injections, 5×10$^4$ cells are injected in 0.5 μL.

Tumor Cell Implantation

The surgical area is prepared by spraying all surfaces with 2% chlorhexidine solution. After using the disinfectant, the following supplies are placed in the surgical area:

Heating pad to maintain mouse body temperature;

Two small Petri dishes; one containing 3% hydrogen peroxide, and one containing 2% chlorhexidine;

Sterile gauze and cotton swabs;

Sterile disposable scalpels; and

Autoclaved surgical stapler.

For anesthesia: a ketamine-xylazine mixture is used. Once a mouse is anesthetized, the scalp is prepared by swabbing several times with a piece of sterile gauze dipped in the chlorhexidine solution. Eye ointment should be applied to maintain adequate moisture during the procedure. Using a sterile scalpel, complete a sagittal incision over the parieto-occipital bone, approximately 1 cm long. The exposed skull surface is then cleaned using a cotton swab soaked in a 3% hydrogen peroxide solution. The bregma should be apparent at this point. Prior to tumor cell injection, use a sterile 25 gauge sharp needle to puncture the skull at 2 mm to the right of the bregma and 1 mm anterior to the coronal suture, thereby creating an opening for the injection of tumor cells. Load the syringe with the desired amount of cell suspension, being careful to avoid creating air bubbles. The outside of syringe should then be cleaned with an alcohol swab to wipe the exterior free of any adherent cells, which will help prevent extracranial tumor establishment and growth. To ensure that the appropriate injection depth is achieved, use a scalpel to cut 3 mm off the pointed end of a P20 pipetteman tip. This section of the tip can be fitted over the syringe and will act to limit the injection depth, and will additionally ensure that the tip of the syringe needle is 3 mm from the underside of the skull. Place the syringe perpendicular to the skull and in the hole previously created, and slowly inject the cell suspension (a 3 μL suspension should be injected over a 1 minute period). Upon completing injection, leave the needle in place for another minute, then slowly withdraw: these steps will help reduce tumor cell reflux. Clean the skull with 3% hydrogen peroxide and dry using a sterile dry cotton swab. Apply sterile bone wax to the hole. Using a forceps, draw the scalp together over the skull and staple to close. For optimal healing, the scalp should be stapled with the dermis of each side of the scalp against each other (underside against underside). The stapled scalp should be cleaned using Chlorhexidine solution, and buprenorphine then administered by subcutaneous injection for post-operative pain relief. Monitor all mice post-operatively until they become ambulant and retain normal activity. Typically, recovery time is around 30 minutes.

Drug Administration and Analysis.

The treatment groups are comprised at least 8 animals for increasing the statistical certainty of conclusions regarding tumor response, or lack thereof, to therapy. After pre-determined days based on literature, 3 Doses of testing compound, one dose of afatinib (20 mg/kg), and one dose of BCNU (20 mg/square meter) are administered orally via oral gavage. A controlled vehicle groups is also maintained. For survival analysis, the Kaplan-Meier estimator is used, and from which survival curves are generated, and median survival values determined. Differences between survival curves are compared using a log-rank test.

Example 16

Pharmacokinetics Studies

Sample preparation: The test article each was dissolved in 10% DMSO and 90% of (40% HP-β-CD in deionized water) to yield concentration at 2 mg/mL for intravenous and oral administration.

Method development and plasma samples analysis were performed by Analytical Sciences Division of the Testing Facility by means of LC-MS/MS. The analytical results were confirmed using quality control samples for intra-assay variation (within day variation). The accuracy of >66% of the quality control samples was between 80-120% of the known value(s).

Each group consisted of 3 male Sprague Dawley rats (7-8 week old, 200-300 g body weight). The test articles were administered by a single bolus intravenous injection via the lateral tail vein or via oral gavage.

Blood samples (approximately 300 μl) were collected via retro-orbital puncture after anaesthesia using mixed gas ($CO_2:O_2=7:3$) into tubes containing EDTA-K3 anticoagulant at appropriate time points. 10 time points (Groups 1-2): Pre-dose and post-dose at 5 min, 15 min, 30 min, 1 h, 2 h, 4 h, 6 h, 8 h and 24 h.

Analysis: The PK blood samples were centrifuged at approximately 8000 rpm for (3 minutes at 2-8° C. and the resulting plasma were separated and stored frozen at approximately −80° C. (following separation, the plasma may be initially placed on ice prior to being stored in the −80° C. freezer). All the plasma samples were labeled with detailed information such as study number, animal number, matrix, time points of collection and date of collection.

Standard set of parameters including Area Under the Curve ($AUC_{(0-t)}$ and $AUC_{(0-\infty)}$), elimination half-live ($T_{1/2}$), maximum plasma concentration ($C_{max}$), time to reach maximum plasma concentration ($T_{max}$), clearance (CL), and volume of distribution ($V_z$) will be calculated using non-compartmental analysis modules in FDA certified pharmacokinetic program WinNonlin Professional v5.2 (Pharsight, USA) by the Study Director. Furthermore, the Bioavailability will be estimated using the following formula:

$$F = \frac{AUC_{(0-\infty)(PO)} \times Dose_{IV}}{AUC_{(0-\infty)(IV)} \times Dose_{(PO)}} \times 100\%$$

Abbreviations $AUC_{(0-t)}$ Area under the curve from the time of dosing to the last measurable concentration $AUC_{(0-\infty)}$ Area under the curve from the time of dosing extrapolated to infinity, based on the last observed concentration CL Total body clearance, CL=Dose/AUC $C_{max}$ Maximum observed concentration, occurring at $T_{max}$ F Bioavailability $MRT_{(0-\infty)}$ Mean residence time from the time of dosing to infinity $T_{max}$ Time of maximum observed concentration $T_{1/2}$ Terminal half-life=$\ln(2)/\lambda z$ $V_z$ Volume of distribution based on the terminal phase Brain concentration: Three rats are for brain collection (2h) only. Three rats are for brain collection (4 h) only. The rest 3 rats are for plasma (9 time points) and brain collection (24h).

Brain Collection and Tissue Processing: Post blood collection, the brain was first perfused intracardially with ~150 mL of ice-cold, 0.1 M Phosphate Buffered Saline (PBS) at pH7.4. Then, the dura was removed before weighing the brain. The brain was then dissected into smaller pieces, rinsed twice with ~10 mL PBS, and then flash frozen on dry ice, and stored at −80° C. before analysis.

Before tissue processing, rat brains were thawed. For the preparation of analytical standards, purchased frozen rat brains (from Pelfreez) were similarly thawed, dissected, rinsed with PBS, and 100 μL of Compound A stock solution (at 500 ng/mL and 1, 2 5, 10, and 50 μg/mL in acetonitrile) was spiked directly into the tissue. Both Compound A dosed and spiked brains then underwent the same processing procedures described below.

Briefly, 2 mL of water was added to each brain before homogenization. Homogenize the brain in 2 to 3 sessions, each approximately 15 sec. The mechanical probe of the homogenizer was cleansed in water, 70% ethanol, and ethyl acetate after each sample. The resulting brain homogenates were then extracted with ethyl acetate three times (14 mL total), and centrifuged to separate the aqueous and organic phases after each extraction. Per brain, pooled organic phase were evaporated under a stream of nitrogen at 40° C. and the residues were reconstituted with 4 mL of mobile phase B. Compound A spiked brain samples in the 4 mL solutions had final concentrations of 12.5, 25, 50, 125, 250, 1250 ng/mL. The reconstituted samples were incubated for ~15 minutes at 60° C. and, vortexed for 10 minutes to fully dissolve the analytes. The samples were centrifuged, and then further diluted with Mobile phase B (shown below) before LC/MS/MS analysis. Dilute 20 μL of reconstituted samples with 1.5 mL mobile phase B. Transfer and inject supernatant to LC/NIS/MS system for analysis.

Figure 3:
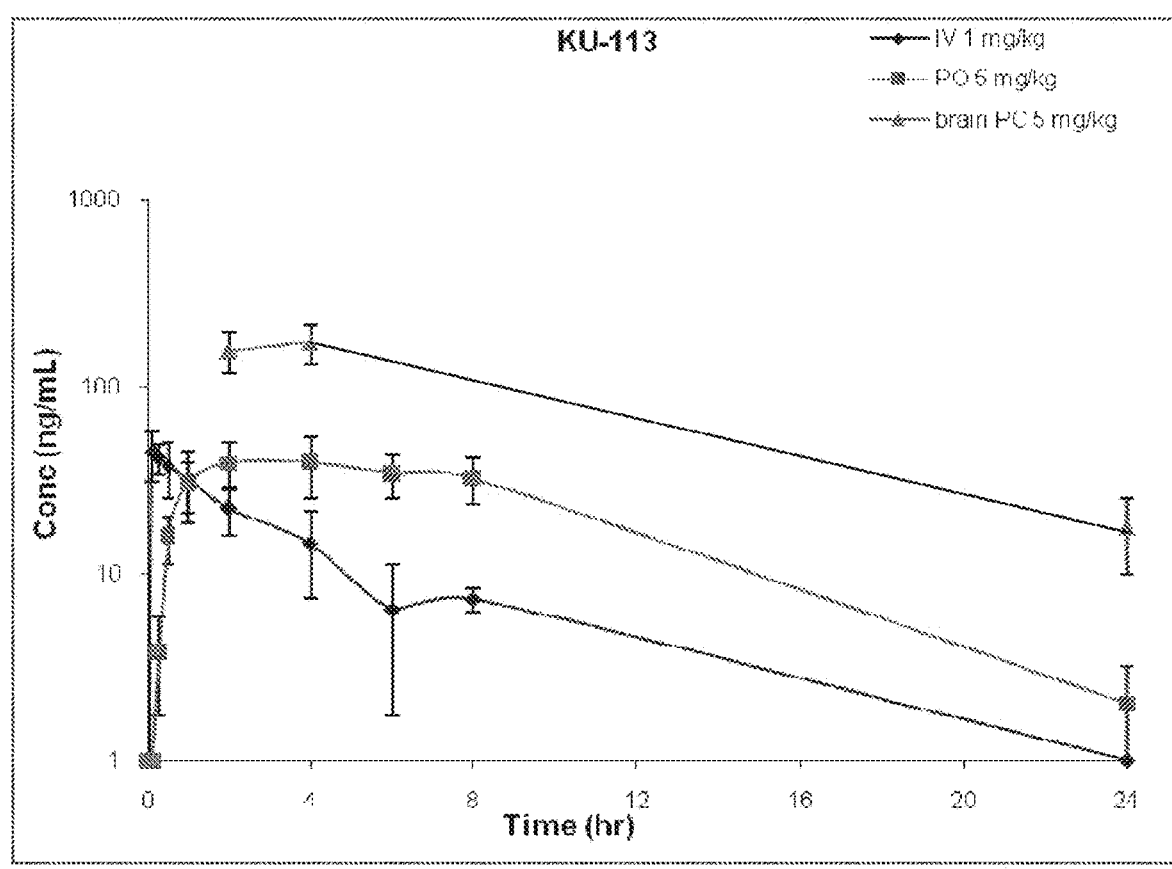
FIG. 3 shows the rat pharmacokinetics data for Compound KU113 with brain concentration.

Rat pharmacokinetics (PK) of Compound KU113 (Example 4), with brain concentration, is shown in FIG. 3.

Rat PK parameters measured for Compound. KU113:

| Plasma PK Parameters | $C_{max}$ ng/mL | $T_{1/2}$ hr | CL L/h/Kg | $V_z$ L/Kg | $AUC_{0-t}$ ng*hr/mL | $AUC_{0-\infty}$ ng*hr/mL | F % |
|---|---|---|---|---|---|---|---|
| IV 1 mg/Kg | 44.4 | 7.48 | 6.31 | 20.5 | 135 | 158 | 100 |
| PO 5 mg/Kg | 39.3 | 14.86 | 9.00 | 58.1 | 542 | 555 | 70.1 |

Note:
estimate of oral bioavailability may contain large uncertainty due to the flat nature of the PO data at the last three observable data points. As a comparison, if using AUC(0-t) instead of AUC(0-∞), the calculated oral bioavailability becomes 80.5%.

Brain concentration measured for Compound KU113

| | P.O. 5 mg/Kg | | | | | |
|---|---|---|---|---|---|---|
| Time | Conc. (ng/g) | | | | | B/P |
| (hr) | No. 1 | No. 2 | No. 3 | Mean | SD | ratio |
| 2 | 118 | 156 | 194 | 156 | 37.8 | 4.0 |
| 4 | 127 | 209 | 185 | 173 | 42.0 | 4.4 |
| 24 | 26.0 | 11.0 | 15.8 | 17.6 | 7.7 | 8.7 |

Figure 4:
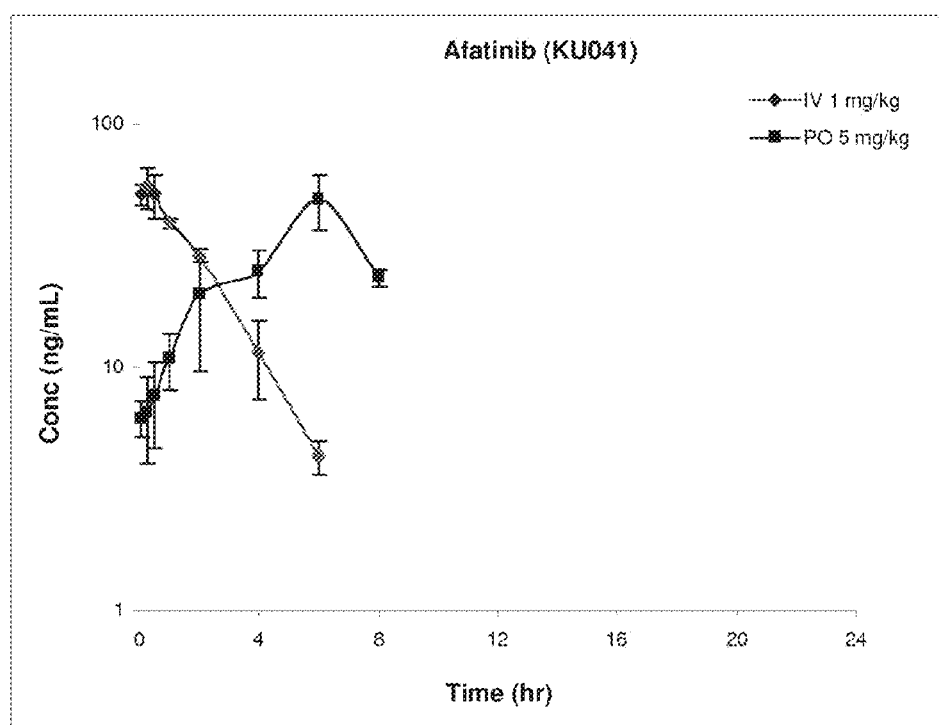
FIG. 4 shows the rat pharmacokinetics data for afatinib (KU041). The brain concentration was below detection limit.

While Compound KU113 showed good oral bioavailability and brain penetration with oral administration, afatinib (bibw-2992), a structurally similar compound, showed poor PK (FIG. 4) and no detectable brain concentration at predetermined time points. Brian/plasma concentration ratio <0.05 (brain concentration <1 ng/g).

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

The disclosures of all patent and scientific literature cited herein are expressly incorporated in their entirety by reference.

What is claimed is:

1. A method for treating breast cancer or gastric cancer in an individual in need thereof comprising administering to the individual an effective amount of a compound of formula (I):

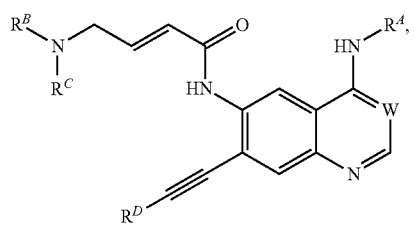

or a salt thereof, wherein:
W is N;
$R^A$ is a substituted aryl or substituted heteroaryl;
each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with 1 to 3 groups independently selected from the group consisting of oxo, halogen and —$OR^1$; or $R^B$ and $R^C$ are taken together with the nitrogen atom to which they are attached to form a 4 to 7-membered heterocyclyl, which is optionally substituted with 1 to 3 groups independently selected from the group consisting of halogen, oxo, —$OR^1$, —$NR^2R^3$, $C_1$-$C_3$ alkyl and $C_3$-$C_6$ cycloalkyl;
$R^D$ is a heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl; and
each $R^1$, $R^2$ and $R^3$ is independently selected from H and $C_1$-$C_3$ alkyl.

2. The method of claim 1, wherein the breast cancer or gastric cancer is an erlotinib-resistant cancer.

3. A method of treating a brain tumor in an individual in need thereof comprising administering to the individual an effective amount of a compound of formula (I):

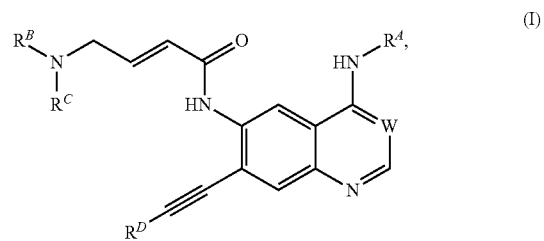

or a salt thereof, wherein:
W is N;
$R^A$ is a substituted aryl or substituted heteroaryl;
each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with 1 to 3 groups independently selected from the group consisting of oxo, halogen and —$OR^1$; or $R^B$ and $R^C$ are taken together with the nitrogen atom to which they are attached to form a 4 to 7-membered heterocyclyl, which is optionally substituted with 1 to 3 groups independently selected from the group consisting of halogen, oxo, —$OR^1$, —$NR^2R^3$, $C_1$-$C_3$ alkyl and $C_3$-$C_6$ cycloalkyl;
$R^D$ is a heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl; and
each $R^1$, $R^2$ and $R^3$ is independently selected from H and $C_1$-$C_3$ alkyl.

4. A method of preventing or delaying the development of brain metastasis of a cancer in an individual in need thereof comprising administering to the individual an effective amount of a compound of formula (I):

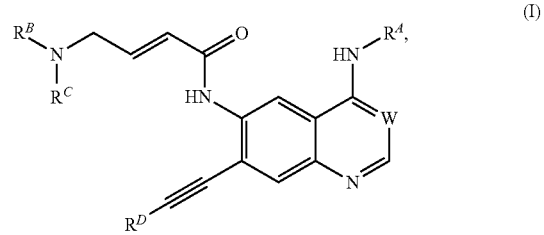

or a salt thereof, wherein:
W is N;
$R^A$ is a substituted aryl or substituted heteroaryl;
each $R^B$ and $R^C$ is independently H, $C_1$-$C_3$ alkyl or $C_3$-$C_6$ cycloalkyl, where each of the $C_1$-$C_3$ alkyl and $C_3$-$C_6$ cycloalkyl is optionally substituted with 1 to 3 groups independently selected from the group consisting of oxo, halogen and —$OR^1$; or $R^B$ and $R^C$ are taken together with the nitrogen atom to which they are attached to form a 4 to 7-membered heterocyclyl, which is optionally substituted with 1 to 3 groups independently selected from the group consisting of halogen, oxo, —$OR^1$, —$NR^2R^3$, $C_1$-$C_3$ alkyl and $C_3$-$C_6$ cycloalkyl;
$R^D$ is a heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —OCF3, —OR$^1$, —CF$_3$, —NR$^2$R$^3$, C$_1$-C$_3$ alkyl and C$_3$-C$_6$ cycloalkyl; and each R$^1$, R$^2$ and R$^3$ is independently selected from H and C$_1$-C$_3$ alkyl.

5. The method of claim 3, wherein the brain tumor is a primary brain tumor.

6. The method of claim 5, wherein the brain tumor is a glioma.

7. The method of claim 5, wherein the brain tumor is glioblastoma multiforme.

8. The method of claim 3, wherein R$^A$ is a substituted aryl.

9. The method of claim 8, wherein R$^A$ is a substituted phenyl.

10. The method of claim 9, wherein R$^A$ is a substituted phenyl selected from the group consisting of:

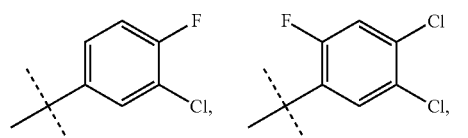

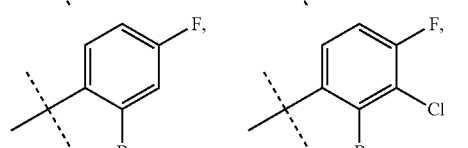

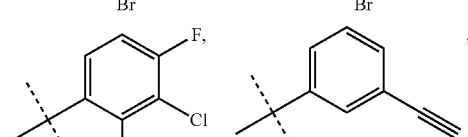

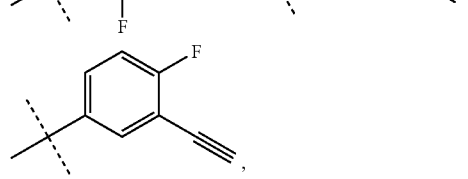

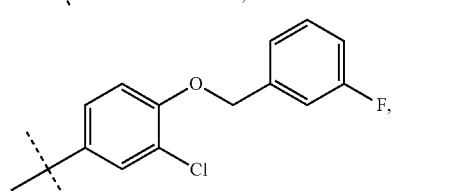

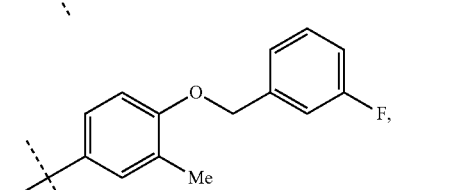

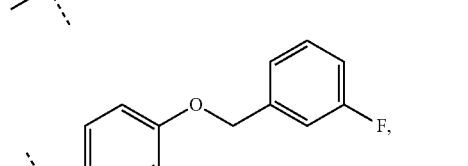

-continued

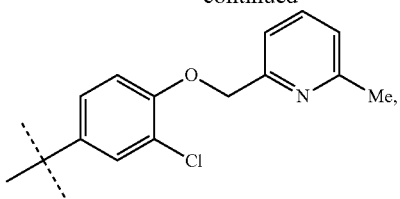

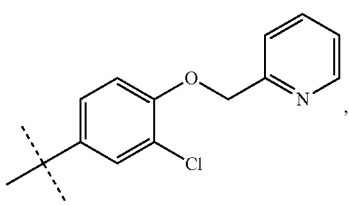

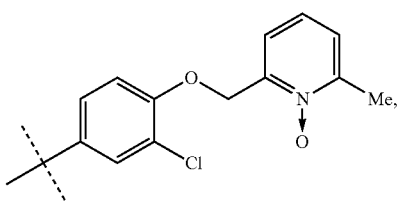

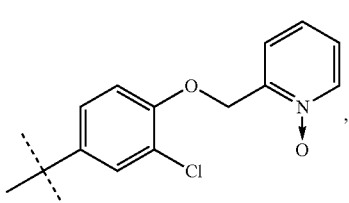

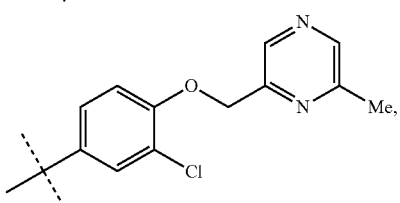

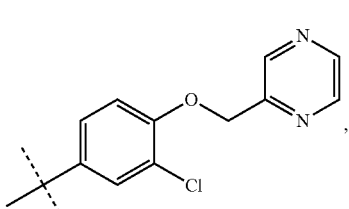

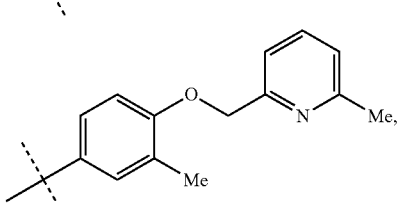

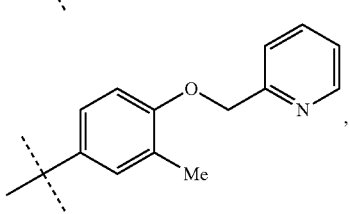

-continued

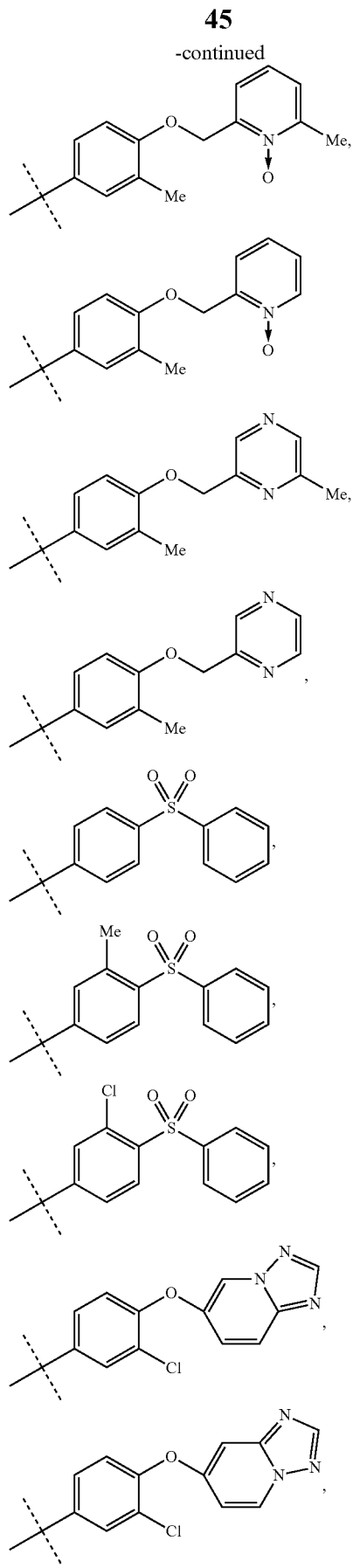

-continued

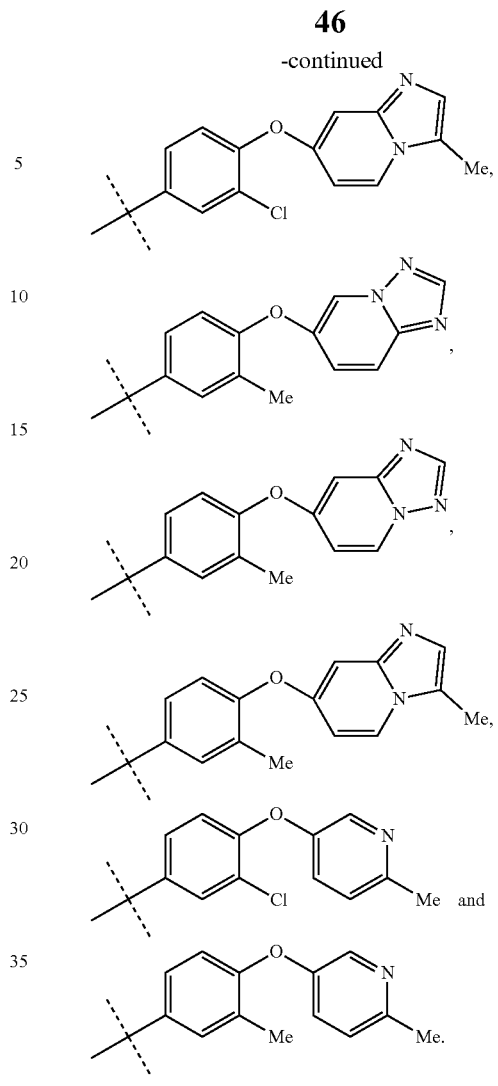

11. The method of claim 9, wherein $R^A$ is 3-chloro-4-fluorophenyl.

12. The method of claim 3, wherein $R^A$ is a substituted heteroaryl.

13. The method of claim 8, wherein each $R^B$ and $R^C$ is independently H, $C_1$-$C_3$ alkyl or $C_3$-$C_6$ cycloalkyl.

14. The method of claim 13, wherein each $R^B$ and $R^C$ is independently $C_1$-$C_3$ alkyl.

15. The method of claim 14, wherein each $R^B$ and $R^C$ is methyl.

16. The method of claim 3, wherein each $R^B$ and $R^C$ is independently H or $C_1$-$C_3$ alkyl optionally substituted with 1 to 3 groups independently selected from the group consisting of oxo, halogen and —$OR^1$.

17. The method of claim 3, wherein $R^B$ and $R^C$ are taken together with the nitrogen atom to which they are attached to form a 4 to 7-membered heterocyclyl, which is optionally substituted with up to 3 groups independently selected from the group consisting of halogen, oxo, —$OR^1$, —$NR^2R^3$, $C_1$-$C_3$ alkyl and $C_3$-$C_6$ cycloalkyl.

18. The method of claim 3, wherein $R^D$ is a 4 to 10-membered heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl.

19. The method of claim 18, wherein $R^D$ is a 5 or 6-membered heterocyclyl containing one annular hetero atom.

20. The method of claim 19, wherein $R^D$ is tetrahydrofuran-3-yl, 3-oxabicyclo[3.1.0]hexan-6-yl or 3-oxabicyclo[3.1.0]hexan-1-yl.

21. The method of claim 20, wherein $R^D$ is 3-oxabicyclo[3.1.0]hexan-6-yl.

22. The method of claim 3, wherein the compound of formula (I) is selected from the group consisting of:
- (E)-N-(4-(3-chloro-4-fluorophenylamino)-7-(2-(tetrahydrofuran-3-yl)ethynyl) quinazolin-6-yl)-4-(dimethylamino)but-2-enamide,
- (E)-N-(4-(3 -chloro-4-fluorophenylamino)-7-(2-((S)-tetrahydrofuran-2-yl)ethynyl) quinazolin-6-yl)-4-(dimethylamino)but-2-enamide,
- (E)-N-(4-(3 -chloro-4-fluorophenylamino)-7-(2-((R)-tetrahydrofuran-2-yl)ethynyl) quinazolin-6-yl)-4-(dimethylamino)but-2-enamide,
- (E)-N-(4-(3 -chloro-4-fluorophenylamino)-7-(2-((1R, 5S,6s)-3-ox a-bicyclo [3.1.0] hexan-6-yl)ethynyl)quinazolin-6-yl)-4-(dimethylamino)but-2-enamide,
- (E)-N-(4-(3 -chloro-4-fluorophenylamino)-7-(2-(3 -oxabicyclo [3.1.0] hexan-1-yl)ethynyl) quinazolin-6-yl)-4-(dimethylamino)but-2-enamide,
- (E)-N-(4-(3 -chloro-4-fluorophenylamino)-7-(2-((1R, 5S)-3-ox a-bicyclo [3.1.0] hexan-1-yl)ethynyl)quinazolin-6-yl)-4-(dimethylamino)but-2-enamide, and
- (E)-N-(4-(3-chloro-4-fluorophenylamino)-7-(2-((1S, 5R)-3-ox a-bicyclo [3.1.0] hexan-1-yl)ethynyl)quinazolin-6-yl)-4-(dimethylamino)but-2-enamide.

23. The method of claim 3, wherein the compound is of the formula:

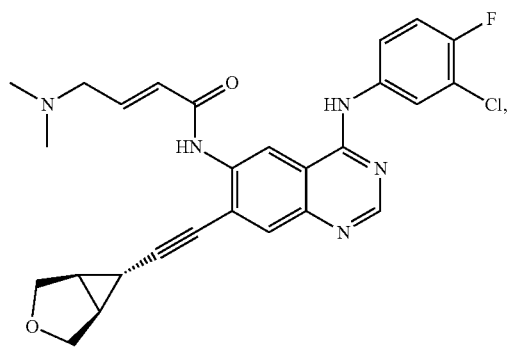 [SMILES: CN(C)C/C=C/C(=O)Nc1cc2c(Nc3ccc(F)c(Cl)c3)ncnc2cc1C#C[C@@H]1[C@H]2COC[C@@H]12]

or a salt thereof.

24. The method of claim 1, wherein $R^4$ is a substituted aryl.

25. The method of claim 24, wherein $R^4$ is a substituted phenyl.

26. The method of claim 25, wherein $R^4$ is a substituted phenyl selected from the group consisting of:

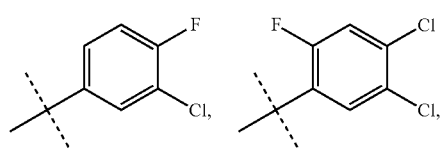

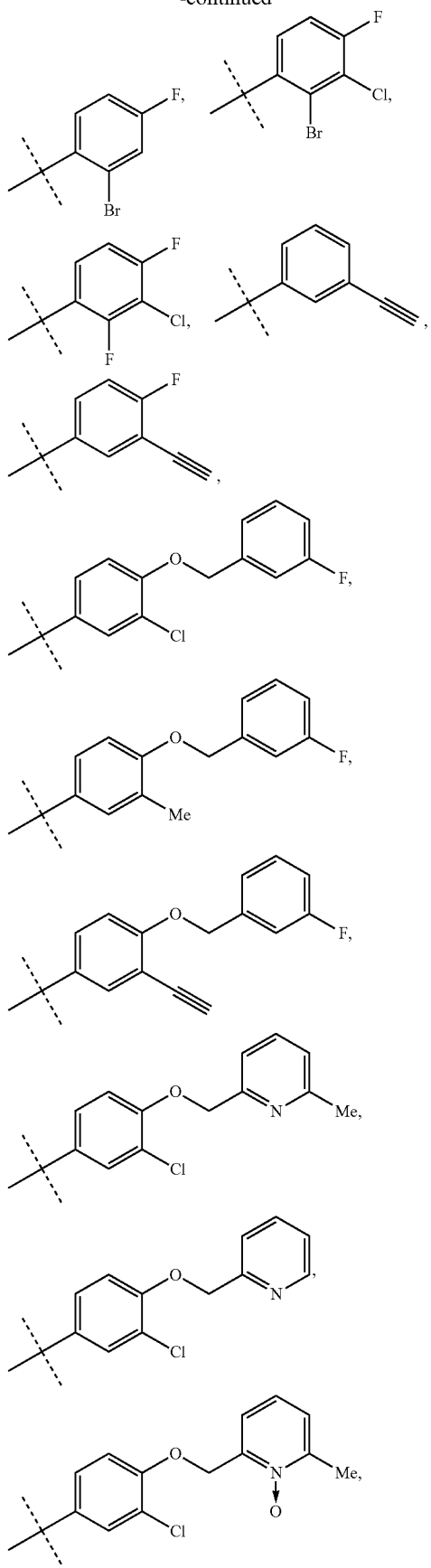

-continued
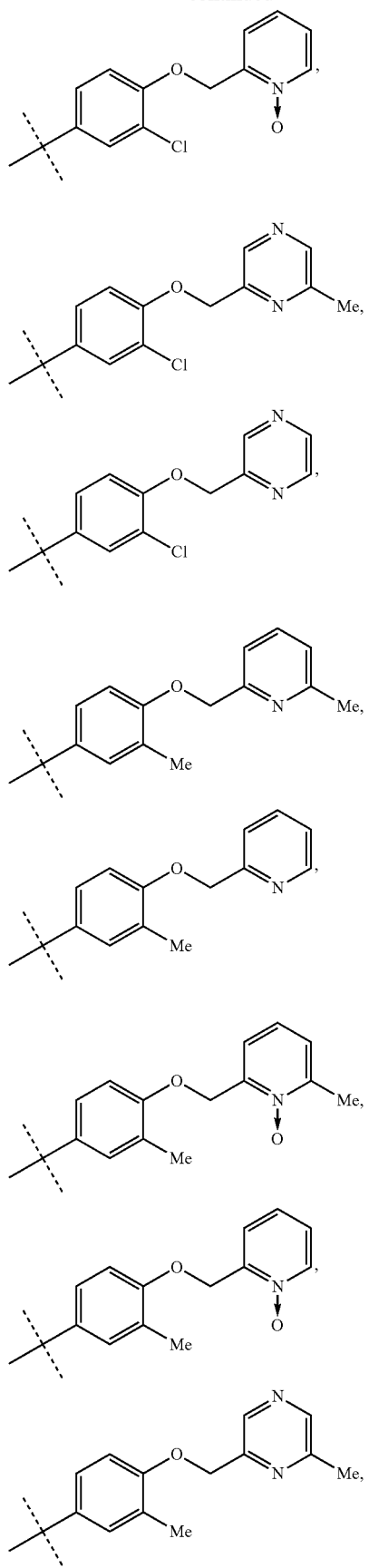
-continued
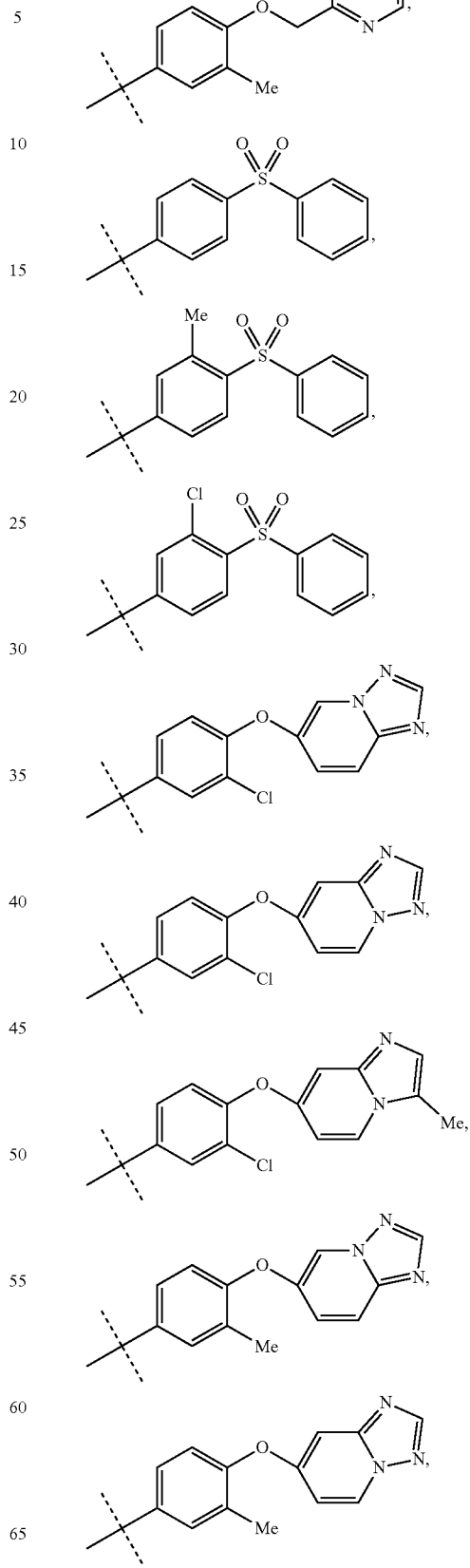

-continued

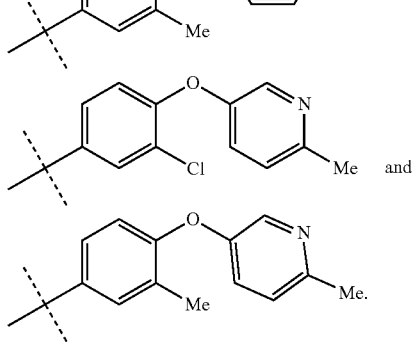

27. The method of claim 25, wherein $R^A$ is 3-chloro-4-fluorophenyl.
28. The method of claim 1, wherein $R^A$ is a substituted heteroaryl.
29. The method of claim 24, wherein each $R^B$ and $R^C$ is independently H, $C_1$-$C_3$ alkyl or $C_3$-$C_6$ cycloalkyl.
30. The method of claim 29, wherein each $R^B$ and $R^C$ is independently $C_1$-$C_3$ alkyl.
31. The method of claim 30, wherein each $R^B$ and $R^C$ is methyl.
32. The method of claim 1, wherein each $R^B$ and $R^C$ is independently H or $C_1$-$C_3$ alkyl optionally substituted with 1 to 3 groups independently selected from the group consisting of oxo, halogen and —$OR^1$.
33. The method of claim 1, wherein $R^B$ and $R^C$ are taken together with the nitrogen atom to which they are attached to form a 4 to 7-membered heterocyclyl, which is optionally substituted with up to 3 groups independently selected from the group consisting of halogen, oxo, —$OR^1$, —$NR^2R^3$, $C_1$-$C_3$ alkyl and $C_3$-$C_6$ cycloalkyl.
34. The method of claim 1, wherein $R^D$ is a 4 to 10-membered heterocyclyl containing 1 to 3 hetero ring atoms selected from "O", "N", "S", S(O)", or "S(O)$_2$", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl.
35. The method of claim 34, wherein $R^D$ is a 5 or 6-membered heterocyclyl containing one annular hetero atom.
36. The method of claim 35, wherein $R^D$ is tetrahydrofuran-3-yl, 3-oxabicyclo[3.1.0]hexan-6-yl or 3-oxabicyclo[3.1.0]hexan-1-yl.
37. The method of claim 36, wherein $R^D$ is 3-oxabicyclo[3.1.0]hexan-6-yl.
38. The method of claim 1, wherein the compound of formula (I) is selected from the group consisting of:
   (E)-N-(4-(3-chloro-4-fluorophenylamino)-7-(2-(tetrahydrofuran-3-yl)ethynyl) quinazolin-6-yl)-4-(dimethylamino)but-2-enamide,
   (E)-N-(4-(3 -chloro-4-fluorophenylamino)-7-(2-((S)-tetrahydrofuran-2-yl)ethynyl) quinazolin-6-yl)-4-(dimethylamino)but-2-enamide,
   (E)-N-(4-(3 -chloro-4-fluorophenylamino)-7-(2-((R)-tetrahydrofuran-2-yl)ethynyl) quinazolin-6-yl)-4-(dimethylamino)but-2-enamide,
   (E)-N-(4-(3 -chloro-4-fluorophenylamino)-7-(2-((1R,5S,6s)-3-ox a-bicyclo [3.1.0] hexan-6-yl)ethynyl)quinazolin-6-yl)-4-(dimethylamino)but-2-enamide,
   (E)-N-(4-(3 -chloro-4-fluorophenylamino)-7-(2-(3 -oxabicyclo [3.1.0] hexan-1-yl)ethynyl) quinazolin-6-yl)-4-(dimethylamino)but-2-enamide,
   (E)-N-(4-(3 -chloro-4-fluorophenylamino)-7-(2-((1R,5S)-3-ox a-bicyclo [3.1.0] hexan-1-yl)ethynyl)quinazolin-6-yl)-4-(dimethylamino)but-2-enamide, and
   (E)-N-(4-(3 -chloro-4-fluorophenylamino)-7-(2-((1S,5R)-3-ox a-bicyclo [3.1.0] hexan-1-yl)ethynyl)quinazolin-6-yl)-4-(dimethylamino)but-2-enamide.

39. The method of claim 1, wherein the compound is of the formula:

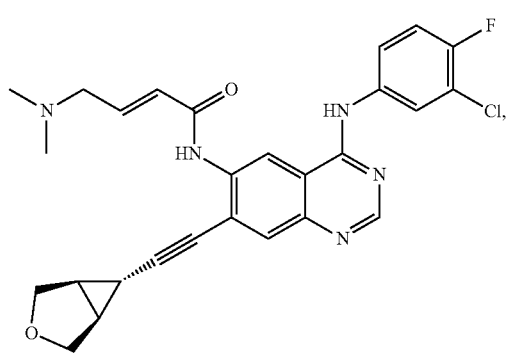 [SMILES: CN(C)C/C=C/C(=O)Nc1cc2c(Nc3ccc(F)c(Cl)c3)ncnc2cc1C#C[C@@H]1[C@H]2COC[C@@H]12]

or a salt thereof.

40. The method of claim 4, wherein $R^A$ is a substituted aryl.
41. The method of claim 40, wherein $R^A$ is a substituted phenyl.
42. The method of claim 41, wherein $R^A$ is a substituted phenyl selected from the group consisting of:

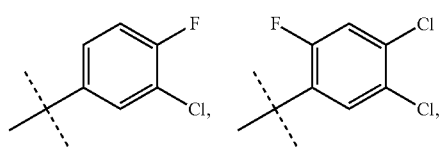

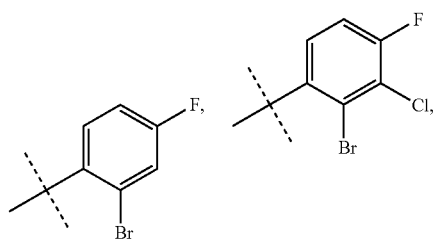

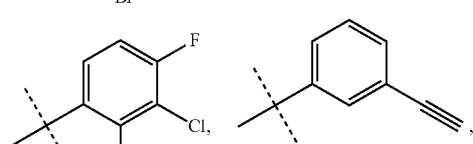

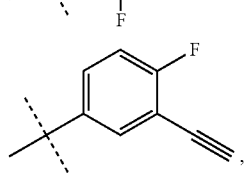

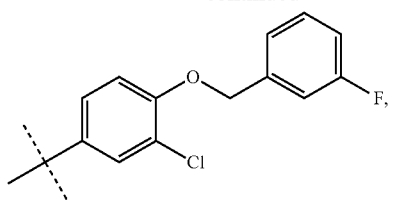
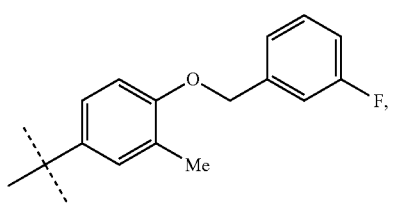
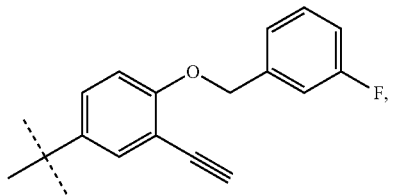
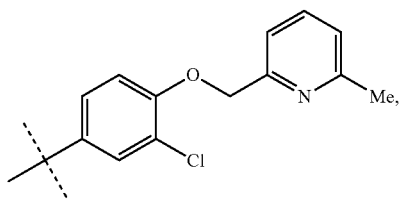
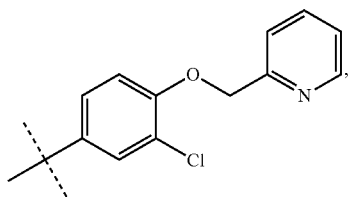
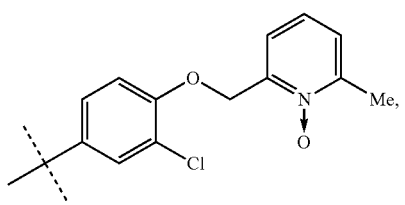
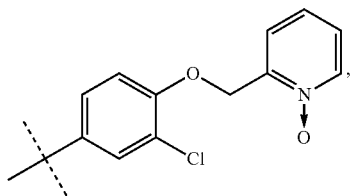
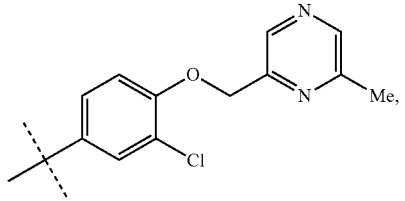
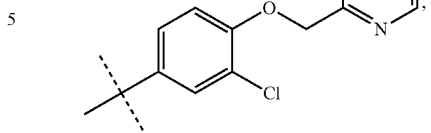
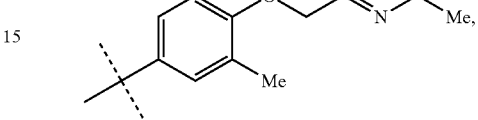
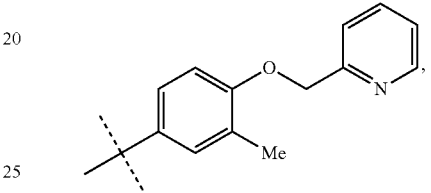
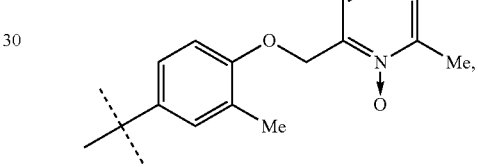
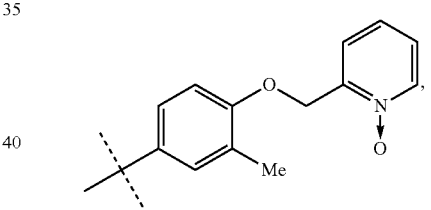
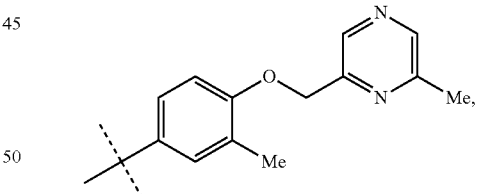
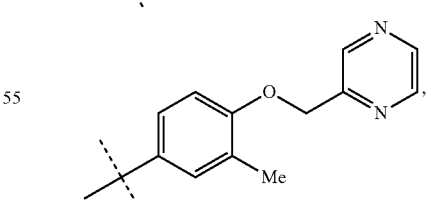
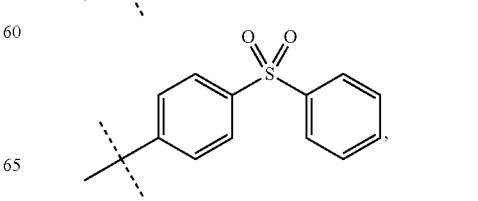

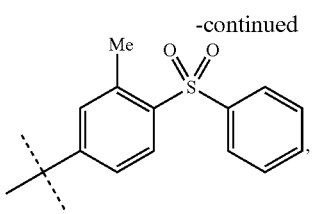
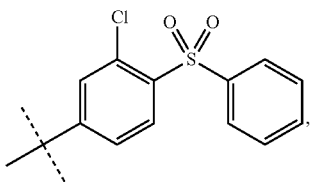
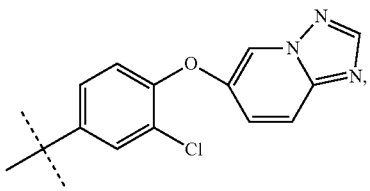
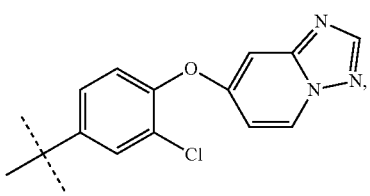
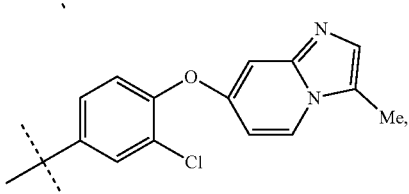
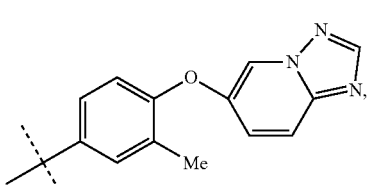
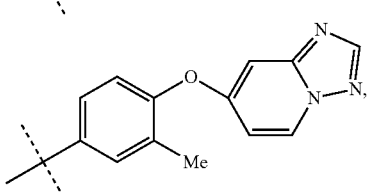
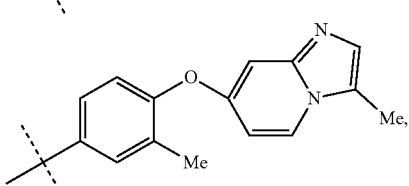
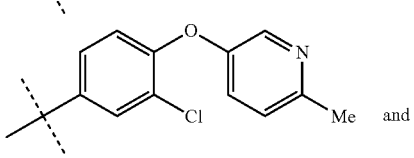

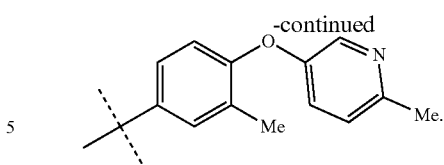

43. The method of claim 41, wherein $R^A$ is 3-chloro-4-fluorophenyl.

44. The method of claim 4, wherein $R^A$ is a substituted heteroaryl.

45. The method of claim 40, wherein each $R^B$ and $R^C$ is independently H, $C_1$-$C_3$ alkyl or $C_3$-$C_6$ cycloalkyl.

46. The method of claim 45, wherein each $R^B$ and $R^C$ is independently $C_1$-$C_3$ alkyl.

47. The method of claim 46, wherein each $R^B$ and $R^C$ is methyl.

48. The method of claim 4, wherein each $R^B$ and $R^C$ is independently H or $C_1$-$C_3$ alkyl optionally substituted with 1 to 3 groups independently selected from the group consisting of oxo, halogen and —$OR^1$.

49. The method of claim 4, wherein $R^B$ and $R^C$ are taken together with the nitrogen atom to which they are attached to form a 4 to 7-membered heterocyclyl, which is optionally substituted with up to 3 groups independently selected from the group consisting of halogen, oxo, —$OR^1$, —$NR^2R^3$, $C_1$-$C_3$ alkyl and $C_3$-$C_6$ cycloalkyl.

50. The method of claim 4, wherein $R^D$ is a 4 to 10-membered heterocyclyl containing 1 to 3 hetero ring atoms selected from "O", "N", "S", S(O)", or "S(O)2", where the heterocyclyl is optionally substituted with 1 to 3 groups independently selected from halogen, oxo, —$OCF_3$, —$OR^1$, —$CF_3$, —$NR^2R^3$, $C_1$-$C_3$ alkyl and $C_3$-$C_6$ cycloalkyl.

51. The method of claim 50, wherein $R^D$ is a 5 or 6-membered heterocyclyl containing one annular hetero atom.

52. The method of claim 51, wherein $R^D$ is tetrahydrofuran-3-yl, 3-oxabicyclo [3.1.0]hexan-6-yl or 3-oxabicyclo [3.1.0]hexan-1-yl.

53. The method of claim 52, wherein $R^D$ is 3-oxabicyclo [3.1.0]hexan-6-yl.

54. The method of claim 4, wherein the compound of formula (I) is selected from the group consisting of:
(E)-N-(4-(3-chloro-4-fluorophenylamino)-7-(2-(tetrahydrofuran-3-yl)ethynyl) quinazolin-6-yl)-4-(dimethylamino)but-2-enamide,
(E)-N-(4-(3-chloro-4-fluorophenylamino)-7-(2-((S)-tetrahydrofuran-2-yl)ethynyl) quinazolin-6-yl)-4-(dimethylamino)but-2-enamide,
(E)-N-(4-(3-chloro-4-fluorophenylamino)-7-(2-((R)-tetrahydrofuran-2-yl)ethynyl) quinazolin-6-yl)-4-(dimethylamino)but-2-enamide,
(E)-N-(4-(3-chloro-4-fluorophenylamino)-7-(2-((1R, 5S,6s)-3-oxa-bicyclo [3.1.0] hexan-6-yl)ethynyl)quinazolin-6-yl)-4-(dimethylamino)but-2-enamide,
(E)-N-(4-(3-chloro-4-fluorophenylamino)-7-(2-(3-oxabicyclo [3.1.0] hexan-1-yl)ethynyl) quinazolin-6-yl)-4-(dimethylamino)but-2-enamide,
(E)-N-(4-(3-chloro-4-fluorophenylamino)-7-(2-((1R, 5S)-3-oxa-bicyclo [3.1.0] hexan-1-yl)ethynyl)quinazolin-6-yl)-4-(dimethylamino)but-2-enamide, and
(E)-N-(4-(3-chloro-4-fluorophenylamino)-7-(2-((1S, 5R)-3-oxa-bicyclo [3.1.0] hexan-1-yl)ethynyl)quinazolin-6-yl)-4-(dimethylamino)but-2-enamide.

55. The method of claim 4, wherein the compound is of the formula:
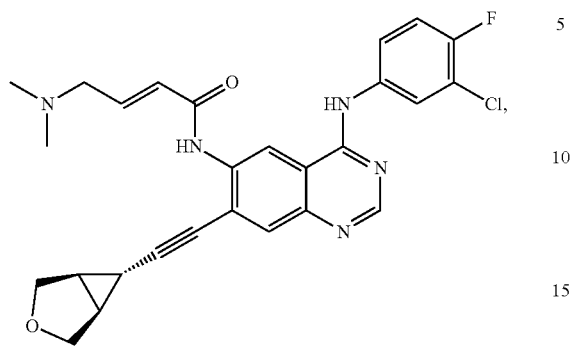
or a salt thereof.